United States Patent [19]

Ward et al.

[11] Patent Number: 4,978,675
[45] Date of Patent: Dec. 18, 1990

[54] MACROLIDE ANTIBIOTICS AND THEIR PREPARATION

[75] Inventors: John B. Ward, Bushey; Hazel M. Noble, Burnham; Neil Porter, Pinner; Richard A. Fletton, Ruislip; David Noble, Burnham; Derek R. Sutherland, Chalfont St Giles; Michael V. J. Ramsay, South Harrow, all of England

[73] Assignee: American Cyanamid Company, Stamford, Conn.

[21] Appl. No.: 119,347

[22] Filed: Nov. 10, 1987

Related U.S. Application Data

[63] Continuation of Ser. No. 855,450, Apr. 24, 1986, abandoned.

[30] Foreign Application Priority Data

| | | |
|---|---|---|
| Apr. 30, 1985 [GB] | United Kingdom | 8510942 |
| Apr. 30, 1985 [GB] | United Kingdom | 8510943 |
| Apr. 30, 1985 [GB] | United Kingdom | 8510944 |
| Mar. 12, 1986 [GB] | United Kingdom | 8606103 |

[51] Int. Cl.$^5$ ................. A61K 31/335; C07D 313/00
[52] U.S. Cl. ........................ 514/450; 549/264
[58] Field of Search ..................... 549/264, 450

[56] References Cited

U.S. PATENT DOCUMENTS

| | | | |
|---|---|---|---|
| 4,201,861 | 5/1980 | Mrozik et al. | 536/7.1 |
| 4,289,760 | 9/1981 | Mrozik et al. | 536/7.1 |
| 4,423,209 | 12/1983 | Mrozik | 549/264 |
| 4,457,920 | 7/1984 | Mrozik | 549/264 |
| 4,550,160 | 10/1985 | Mrozik | 536/7.1 |

FOREIGN PATENT DOCUMENTS

170006 2/1986 European Pat. Off.

OTHER PUBLICATIONS

Abstract of JA 84/16894.
Abstract of JA 84/20284.

*Primary Examiner*—Glennon H. Hollrah
*Assistant Examiner*—Amelia A. Owens
*Attorney, Agent, or Firm*—Bacon & Thomas

[57] ABSTRACT

Compounds are described of formula (II)

and salts thereof, wherein
$R^1$ reprsents a methyl, ethyl or isopropyl group;
$R^2$ represents a hydrogen atom or a group $OR^5$ (where $OR^5$ is a hydroxy group or a substituted hydroxyl group having up to 25 carbon atoms) and $R^3$ represents a hydrogen atom, or $R^2$ and $R^3$ together with the carbon atom to which they are attached represent a $>C=O$ group; and
$OR^4$ represnts a group $OR^5$ as defined above;

with the proviso that when $R^2$ represents a hydroxy group $OR^4$ represents a substituted hydroxy group other than a methoxy group.

These compounds may be used for controlling insect, acarine, nematide or other pests.

27 Claims, No Drawings

MACROLIDE ANTIBIOTICS AND THEIR PREPARATION

This application is a continuation of application Ser. No. 855,450, filed Apr. 24, 1986 now abandoned.

This invention relates to novel antibiotic compounds and to processes for their preparation.

In our United Kingdom Patent Application No. 8522699 we describe the production of Antibiotics S541 which may be isolated from the fermentation products of a novel Streptomyces sp. Antibiotics S541 are a group of related compounds having the partial formula (I)

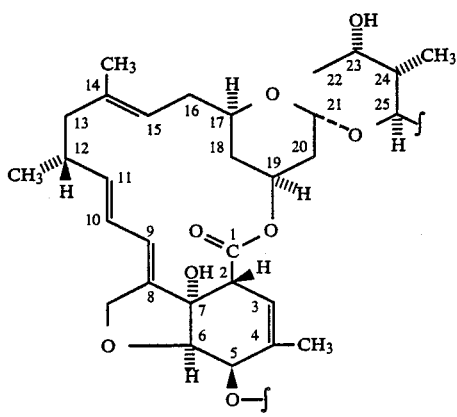

We have now found a further group of compounds with antibiotic activity which may he prepared by chemical modification of Antibiotics 5541 or by isolation from a culture of a microorganism of the genus Streptomyces as described herein. The novel compounds of the invention have antibiotic activity and/or are of use as intermediates. In the preparation of other active compounds and/or in the isolation and purification of Antibiotics S541 compounds.

The compounds of the invention are the 23-ketone, 23-deoxy and 23-hydroxyl or substituted hydroxyl analogues of Antibiotics S541 having a hydroxyl or substituted hydroxyl group at the 5-position.

Thus in one aspect, the invention particularly provides the compounds of formula (II)

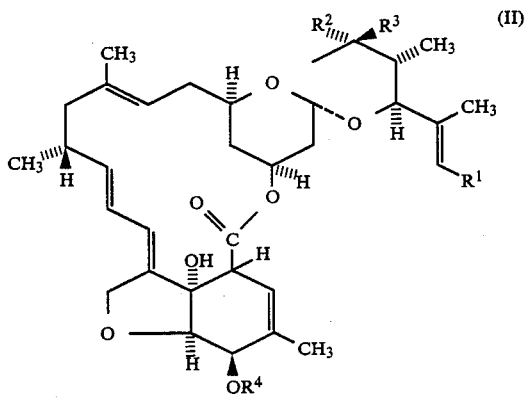

wherein $R^1$ represents a methyl, ethyl or isopropyl group $R^2$ represents a hydrogen atom or a group $OR^5$ (where $OR^5$ is a hydroxy group, or a substituted hydroxyl group having up to 25 carbon atoms) and $R^3$ represents a hydrogen atom, or $R^2$ and $R^3$ together with the carbon atom to which they are attached represent a $>C=O$ group; and $OR^4$ represents a group $OR^5$ as defined above, and the salts thereof with the proviso that when $R^2$ represents a hydroxy group then $OR^4$ represents a substituted hydroxy group other than a methoxy group.

When the compounds of formula (I) are to be used as intermediates, one or both of the groups $R^2$ and $-OR^4$ will often be a protected hydroxy group and the invention particularly includes such protected compounds.

When the groups $R^2$ or $OR^4$ in compounds of formula (I) are substituted hydroxyl groups they may be the same or different and may represent acyloxy groups [e.g. a group of the formula $-OCOR^6$, $-OCO_2R^6$ or $-OCSOR^6$ (where $R^6$ is an aliphatic, araliphalic or aromatic group, for example an alkyl, alkenyl, alkynyl cycloalkyl, aralkyl or aryl group)], a formyloxy group, a group $-OR^7$ (where $R^7$ is as defined above for $R^6$), a group $-OSO_2R^8$ (where $R^8$ is a $C_{1-4}$ alkyl or $C_{6-10}$ aryl group), a silyloxy group, a cyclic or acyclic acetaloxy group or a group $OCO(CH_2)_nCO_2R^9$ (where $R^9$ is a hydrogen atom or a group as defined for $R^6$ above and n represents zero, 1 or 2).

Where $R^6$ or $R^7$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^6$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^7$ is a substituted alkyl group it may be substituted by a $C_{3-7}$ cycloalkyl e.g. cyclopropyl group.

Where $R^6$ or $R^7$ are alkenyl or alkynyl groups, they may be for example $C_{2-8}$ alkenyl, e.g. allyl, or $C_{2-8}$ alkynyl groups.

Where $R^6$ or $R^7$ are cycloalkyl groups, they may be for example $C_{3-12}$ cycloalkyl, such as $C_{3-7}$ cycloalkyl. Thus $R^6$ may be for example a cyclopropyl, cyclobutyl, cyclopentyl or cyclohexyl group. $R^7$ may be for example a cyclopentyl group.

Where $R^6$ or $R^7$ are aralkyl groups, they preferably have 1 to 6 carbon atoms in the alkyl moiety and the aryl group(s) may be carbocyclic or heterocyclic and preferably contain 4–15 carbon atoms e.g. phenyl. Examples of such groups include phen$C_{1-6}$alkyl, e.g. benzyl or phenethyl groups.

Where $R^6$ and $R^7$ are aryl groups, they may be carbocyclic or heterocyclic and preferably have 4–15 carbon atoms, and may be for example a phenyl group.

When $R^2$ or $-OR^4$ is a group $-OSO_2R^8$, it may be for example a methylsulphonyloxy or p-toluenesulphonyloxy group.

Where $R^2$ or $-OR^4$ represents a cyclic acetaloxy group, it may for example have 5–7 ring members and may be for example a tetrahydropyranyloxy group.

When $R^2$ or $-OR^4$ represents a silyloxy group or $R^6$ contains a silyloxy substituent, the silyl group may carry three groups which may be the same or different, selected from alkenyl, alkoxy, cycloalkyl, aralkyl, aryl and aryloxy groups. Such groups may be as defined above for $R^6$ and particularly include methyl, t-butyl and phenyl groups. Particular examples of such silyloxy groups are trimethylsilyloxy and t-butyldimethylsilyloxy.

Where $R^2$ or $OR^4$ represent a group $OCO(CH_2)_nCO_2R^9$, it may for example be a group $OCOCO_2R^9$ OR $OCOCH_2CH_2CO_2R^9$ where $R^9$ represents a hydrogen atom or a $C_{1-4}$ alkyl (e.g. methyl or ethyl) group.

Compounds of formula (II) containing an acidic group may form salts with suitable bases. Examples of such salts include alkali metal salts such as sodium and potassium salts.

An important group of compounds of formula (II) is that in which $R^1$ represents a methyl, ethyl or isopropyl group, $R^2$ and $OR^4$, which may be the same or different, each represent a group $OR^5$ (where $OR^5$ is a hydroxy group or a substituted hydroxy group having up to 25 carbon atoms) and $R^3$ represents a hydrogen atom, and the salts thereof with the proviso that when $R^2$ represents a hydroxy group $OR^4$ represents a substituted hydroxy group other than a methoxy group.

Another important group of compounds of formula (II) is that in which $R^1$ represents a methyl, ethyl or isopropyl group, $R^2$ and $R^3$ together with the carbon atom to which they are attached from a group $\leq C=O$ and $OR^4$ represents a group $OR^5$ (where $OR^5$ is a hydroxy group or a substituted hydroxy group having up to 25 carbon atoms) and the salts thereof.

A further important group of compounds of formula (II) is that in which $R^1$ represents a methyl, ethyl or isopropyl group, $R^2$ and $R^3$ is each a hydrogen atom or $OR^4$ represents a group $OR^5$ (where $OR^5$ represents a hydroxyl or substituted hydroxyl group having up to 25 carbon atoms) and the salts thereof.

In the compounds of formula (II), the group $R^1$ is preferably an isopropyl group.

The group $R^2$ is preferably a hydrogen atom or a hydroxy group or a group of formula $-OCOR^6$ [where $R^6$ is a $C_{1-8}$ alkyl group (optionally substituted by a $C_{1-4}$ alkoxy group) or a phen$C_{1-6}$alkyl group], $-OCO_2R^6$ (where $R^6$ is a $C_{1-8}$ alkyl group optionally substituted by one to three halogen atoms e.g. trichloroethyl), $-OCOCO_2H$, $-OR^7$ (where $R^7$ is a $C_{1-8}$ alkyl, $C_{3-7}$ cycloalkyl, allyl or cyclopropylmethyl group) or $R^2$ and $R^3$ together with the carbon atom to which they are attached form a $>C=O$ group. In particular, $R^2$ is preferably a hydrogen atom or an ethoxy, n-propoxy, n-butoxy, cyclopropylmethoxy, acetoxy, phenacetoxy, propionoxy, isobutyrionoxy or cyclopropanecarbonyloxy group or $R^2$ and $R^3$ together with the carbon atom to which they are attached form a $>C=O$ group.

The group $-OR^4$ in the compounds of formula (II) is preferably a hydroxy, methoxy, acetoxy or methyloxycarbonyloxy group.

Important active compounds according to the invention are those of formula (II) in which $R^1$ is a methyl, ethyl or in particular an isopropyl group, $R^2$ is a hydrogen atom, or an ethoxy, n-propoxy, n-butoxy, acetoxy, or propionoxy group and $R^3$ is a hydrogen atom or $R^2$ and $R^3$ together with the carbon atom to which they are attached form a $>C=O$ group, and $OR^4$ is a hydroxy, acetoxy, or methyloxycarbonyloxy group.

Particularly important active compounds of the invention are those of formula (II) in which:

$R^1$ is an isopropyl group, $R^2$ is a hydrogen atom, $R^3$ is a hydrogen atom an $OR^4$ is a hydroxyl group;

$R^1$ is an isopropyl group, $R^2$ is a propionoxy group, $R^3$ is a hydrogen atom and $OR^4$ is a hydroxyl group;

$R^1$ is an isopropyl group, $R^2$ and $R^3$ together with the carbon atom to which they are attached are $>C=O$ and $-OR^4$ is a hydroxyl group;

$R^1$ is an isopropyl group, $R^2$ is an ethoxy group, $R^3$ is a hydrogen atom and $-OR^4$ is a hydroxyl group; and $R^1$ is an isopropyl group, $R^2$ is a n-propoxy group, $R^3$ is a hydrogen atom and $-OR^4$ is a hydroxyl group.

$R^1$ is a methyl group, $R^2$ is an acetoxy group, $R^3$ is a hydrogen atom and $OR^4$ is a hydroxyl group.

$R^1$ is an ethyl group, $R^2$ is an acetoxy group, $R^3$ is a hydrogen atom and $OR^4$ is a hydroxyl group.

$R^1$ is an isopropyl group, $R^2$ is an acetoxy group, $R^3$ is a hydrogen atom and $OR^4$ is a hydroxyl group.

$R^1$ is an isopropyl group, $R^2$ is a n-butoxy group, $R^3$ is a hydrogen atom and $OR^4$ is a hydroxyl group.

As indicated previously, the compounds according to the invention may be of use as antibiotics and/or as intermediates for the preparation of other active compounds and/or in the isolation and purification of Antibiotics S541 compounds. When the compounds of the invention are to be used as intermediates, the $R^2$ and/or $-OR^4$ groups may be protected hydroxy groups. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Greene. (Wiley-Interscience, New York 1981) and "Protective Groups in Organic Chemistry" by J F W McOmie (Plenum Press, London, 1973). Examples of $R^2$ and $OR^4$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Other active compounds of the invention that are also useful as intermediates are those of formula (II) in which $R^2$ is a $-OCOCO_2H$ group. In particular, these are of use for the isolation and purification of Antibiotics S541 compounds. An especially useful compound is this respect is the compound of formula (II) wherein $R^1$ is an isopropyl group, $R^2$ is the group $-OCOCO_2H$, $R^3$ is a hydrogen atom and $OR^4$ is a hydroxyl group, which may be advantageously used in the isolation and purification of the Antibiotics S541 compound of formula (V) below wherein $R^1a$ is an isopropyl group and R is a hydrogen atom. The compound of formula (V) in an impure form may be converted to the corresponding compound of formula (II) in which $R^2$ is $-OCOCO_2H$ and isolated, e.g. in a crystalline form. The compound of formula (V) may then be regenerated in a substantially purified form from the latter compound using the methods described herein, which isolation and purification methods form further features of the present invention.

Compounds of the invention have antibiotic activity e.g. antihelminthic activity, for example against nematodes, and in particular, anti-endoparasitic and anti-ectoparasitic activity.

Ectoparasites and endoparasites infect humans and a variety of animals and are particularly prevalent in farm animals such as pigs, sheep, cattle, goats and poultry, horses and domestic animals such as dogs and cats. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Nector, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Uncinaria and Wuchareria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Demallenia, Dermatobia, Gastrophilus, Haematobia, Haematopinus, Haemophysalis, Hyalomma, Hyperderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in viro and in vivo against a range of endoparasites and ectoparasites. In particular, we have found that compounds of the invention are active against parasitic nematodes such as *Haemonchus contortus, Ostertagia circumcincta, Trichostrongylus colubiformis, Dictyocaulus viviparis, Cooperia oncophera, Ostertagia ostertagi, Nematospiroides dubius* and *Nippostrongylus braziliensis,* and parasitic mites such as Aarcoptes sp. and Psoroptes sp.

The compounds of the invention are therefore of use in treating animals and humans with endoparasitic and/or ectoparasitic infections.

The species of the parasite will vary according to the host and the predominant site of the infection. Thus, for example *Haemonchus contortus, Ostertagia circumincta* and *Trichostrongylus colubiformis* generally infect sheep and are predominantly located in the stomach and small intestine, whereas *Dictyocaulus viviparus, Cooperia oncophora* and *Ostertagia ostertagi* generally infect cattle and are predominantly located in the lung, intestine or stomach respectively.

The antibiotic activity of compounds of the invention may, for example, be demonstrated b y their activity in vitro against free living nematodes e.g. *Caenorhabiditis elegans.*

Furthermore, compounds of the invention are of use as antifungals, for example, against strains of Candida sp. such as *Candida albicans* and *Candida glabrata* and against yeast such as *Saccharomyces carlsbergenis.*

Compounds of the invention are also of use in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated. Particular examples of such pests are fruit mites and aphides such as *Aphis fabae, Aulacorthum circumflexum Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarisu;* flour beetles such as *Tribolium castaneum;* flies such as *Musca domestica;* fire ants; leaf miners; *Pear psylla; Thrips tabaci;* cockroaches such as *Blatella germanica* and *Periplaneta americana* and mosquitoes such as *Aedes aegypti.*

According to the invention we therefore provide compounds of formula (II) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may be used generally as pesticides to combat or control pests in other circumstances, e.g. in stores, buildings or other public places or location of the pests. In general the compounds may be applied either to the host (animal or human or plants or other vegetation) or to the pests themselves or a locus thereof.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable to pharmaceutically acceptable carriers for use in solid dosage forms include binding agents (e.g. pregelatinised maize starch, polyvinylpyrrolidone or hydroxypropyl methylcellulose); fillers (e.g lactose, micro-crystalline cellulose or calcium phosphate); lubricants (e.g. magnesium stearate, talc or silica); disintegrants (e.g. potato starch or sodium starch glycollate): or wetting agents (e.g. sodium lauryl sulphate). Tablets may be coated by methods well known in the art. Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil oily esters or ethyl alcohol); and preservatives (e.g. methyl or propyl p-hydroxybenzoates or sorbic acid); stabilising and solubilising agents may also be included.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g as part of the daily animal feed or drinking water.

For buccal administration the composition may take the form of tablets, pastes or lozenges formulated in conventional manner.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agent or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000 µg/kg bodyweight preferably from 50–1000 µg/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as for example by blending and/or grinding of the active ingredient(s) together with the carrier or diluent, e.g. solid carrier, solvent or surface active agent.

Suitable solid carriers, for use in formulations such as dusts, granulates and powders may be selected from for example natural mineral fillers, such as diatomite, talc, kaolinite, montmorillonite pyrophylite or attapulgite. Highly dispersed silicic acid or highly dispersed absorbent polymers may, if desired, be included on the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonates acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.001% by weight, for use For use in veterinary medicine or for horticultural and agricultural use and where the compounds of the invention are fermentation derived products, it may be desirable to use the whole fermentation broth, as a source of the active compounds. It may also be suitable to use dried broth (containing mycelia) or to use mycelia separated from the broth and pasteurised or more preferably, dried e.g. by spray-, freeze-, or roller drying. If desired the broth or mycelia may be formulated into compositions including conventional inert carriers, excipients or diluents as described above.

The antibiotic compounds of the invention may be administered or used in combination with other active ingredients.

In particular, the antibiotic compounds of the invention may be used together with Antibiotics S541 compounds or with other antibiotic compounds of the invention. This may occur, for example, where crude fermentation products are reacted according to a process of the invention without prior to subsequent separation; this may be preferable for example in agricultural use of the compounds, where it is important to maintain low production costs.

The compounds of the invention may be prepared by the processes discussed below. In some of these processes it may be necessary to protect a hydroxyl group at the 5- or 23-position in the starting material prior to effecting the reaction described. In such cases it may then be necessary to deprotect the same hydroxyl group once the reaction has occurred to obtain the desired compound of the invention. Conventional protection and deprotection methods may be used, for example as described in the aforementioned books by Greene and McOmie.

Thus, for example, an acyl group such as an acetyl group may be removed by basic hydrolysis e.g. using sodium or potassium hydroxide in aqueous alcohol or by acid hydrolysis e.g. using concentrated sulphuric acid in methanol. Acetal groups such as tetrahydropyranyl may be removed, for example, using acid hydrolysis (using an acid such as acetic or trifluoroacetic acid or a dilute mineral acid). Silyl groups may be removed using fluoride ions (e.g. from a tetraalkylammonium fluoride such as tetra-n-bulylammonium fluoride) hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the presence of a thiol (e.g ethanethiol) in a suitable solvent such as dichloromethane at e.g. room temperature. Selective 5-deprotection of a 5,23-disilyl compound of the invention may be effected using tetra-n-butylammonium fluoride while selective 5-deprotection of a 5,23-diacetoxy compound may be effected using sodium hydroxide in aqueous methanol.

The compounds of the invention in which $R^2$ and/or —$OR^4$ is a substituted hydroxyl group may generally be prepared by reacting Antibiotics S541 compounds (e.g. compounds of formula (V) below) or 5- or 23-O-monosubstituted derivatives thereof with reagents serving to form a substituted hydroxyl group. In general, the 5-hydroxyl group is more reactive than the 23-hydroxyl group. Hydroxyl groups in the 5- position are more readily deprotected than hydroxyl groups in the 23- position. In general, 5-mono-substituted compounds of the invention can be prepared by reacting the 5,23-unsubstituted hydroxy Antibiotics S541 compound with a limited amount of reagent, under milder conditions, while 5,23-disubstituted compounds are formed using larger quantities of reagent and less mild conditions and/or using a catalyst. 23-Mono-substituted compounds of the invention can be prepared by first forming a 5,23-substituted compound and selectively deprotecting at the 5-position. 5,23-Disubstituted compounds of the invention having different substituents at the 5- and 23- positions may be obtained by reacting a compound mono-substituted at either the 5- or 23- position with a reagent serving to form a different substituted hydroxyl group at the other position.

According to a further aspect of the invention we provide a process for the preparation of compounds of formula (II) in which one of $R^2$ and $OR^4$ is a substituted hydroxyl group and the other is a hydroxyl or substituted hydroxyl group as defined above which comprises reacting compounds of formula (111):

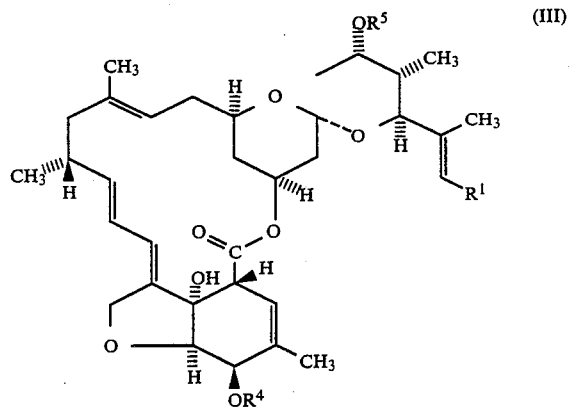

(where $R^1$ is as previously defined and one of —$OR^4$ and—$OR^5$ is a hydroxyl group while the other is a hydroxyl or substituted hydroxyl group) with a reagent serving to convert a hydroxyl group into a substituted hydroxyl group, and if desired followed by selective deprotection of a compound of formula (II) in which $R^2$ and —$OR^4$ are both substituted hydroxyl groups to give a compound of formula (II) in which $OR^4$ is a hydroxyl group and $R^2$ is a substituted hydroxyl group.

The reaction will in general be an acylation, formylation, sulphonylation, etherification, silylation or acetal formation.

Thus, for example, acylation may be effected using an acylating agent such as an acid of formula $R^6COOH$ or a reactive derivative thereof, such as an acid halide (e.g. acid chloride), anhydride or activated ester, or a reactive derivative of a carbonic acid $R^6OCOOH$ or thiocarbonic acid $R^6OCSOH$.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing highly electrophilic acid chlorides (e.g. oxalyl chloride, methoxyacetyl chloride, chloracetyl chloride or bromacelyl chloride) preferably in the presence of an acid scavenger such as calcium carbonate can he used to selectively substitute the 23-position to provide a compound of formula (II) in which $R^2$ is a group $OR^5$ where $R^5$ is a substituted hydroxyl group and $OR^4$ is hydroxyl group. Acylations employing acids are desirably conducted in the presence of a condensing agent, for example a carbodiimide such as N,N'-dicyclohexylcarbodiimide or N-ethyl-N'$\gamma$-dimethylaminooropylcarbodilmide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range $-20°$ to $+100°$ C., e.g. $-10°$ to $+50°$ C.

Formylation may be effected using an activated derivative of formic acid e.g. N-formyl imidazole or formic acetic anhydride under standard reaction conditions.

Sulphonylation may be effected with a reactive derivative of a sulphonic acid $R^8SO_3H$ such as a sulphonyl halide, for example a chloride $R^8SO_2Cl$ or a sulphonic anhydride. The sulphonylation is preferably effected in the presence of a suitable acid binding agent as described above.

Etherification may be effected using a reagent of formula $R^7Y$ (where $R^7$ is as previously defined and Y represents a leaving group such as chlorine, bromine or iodine atom or a hydrocarbylsulphonyloxy group, such as mesyloxy or tosyloxy, or a haloalkanoyloxy group such as dichloroacetoxy). The reaction may be carried out by formation of a magnesium alkoxide using a Grignard reagent such as a methylmagnesium halide e.g. methylmagnesium iodide or using a trialkylsilylmethylmagnesium halide e.g. trimethylsilylmethylmagnesium chloride followed by treatment with the reagent $R^7Y$.

Alternatively, the reaction may be effected in the presence of a silver salt such as silver oxide, silver perchlorate, silver carbonate or silver salicylate or mixtures thereof, and this system may be particularly appropriate when etherification is carried cut using an alkyl halide (e.g. methyl iodide)

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Non-aqueous solvents which may be employed in the above reactions include ketones (e.g. acetone), amides (e.g. N,N-dimethylformamide, N,N-dimethylacetamide or hexamethylphosporamide), ethers (e.g. cyclic ethers such as tetrahydrofuran or dioxan, and acyclic ethers such as dimethoxyethane or diethylether), nitriles (e.g. acetonitrile), hydrocarbons such as halogenated hydrocarbons (e.g. methylene chloride), and esters such as ethyl acetate, as well as mixtures of two or more such solvents.

Silylation may be effected by reaction with a silyl halide (e.g. chloride), advantageously in the presence of a base such as imidazole triethylamine or pyridine, using a solvent such as dimethylformamide.

In many instances, for example, where a 5,23-dihydroxy compound of formula (III) is used as starting material, a mixture of final products e.g. a mixture of 5-monosubstituted and 5,23-disubstituted derivatives will be formed. These can, however, be separated by conventional techniques, e.g. chromatography, for example silica chromatography or hplc.

In a further process according to the invention a compound of formula (II) in which $R^2$ and $R^3$ each represents a hydrogen atom may be prepared by reaction of a compound of formula (III) in which $R^1$ is as previously defined and $OR^4$ is a substituted hydroxyl group and $OR^5$ is a hydroxyl group by replacement of the 23-hydroxy group with a hydrogen atom followed by deprotection of the group $OR^4$ where a compound in which $OR^4$ is hydroxyl group is required, and, if desired, followed by resubstitution to give a compound of formula (II) in which $OR^4$ is a substituted hydroxyl group.

Thus, the starting materials of formula (III) in which $OR^4$ is a substituted hydroxyl group and $OR^5$ is a hydroxyl group may be reacted with a reagent serving to replace the hydroxyl group with a leaving group to give compounds of formula (IV)

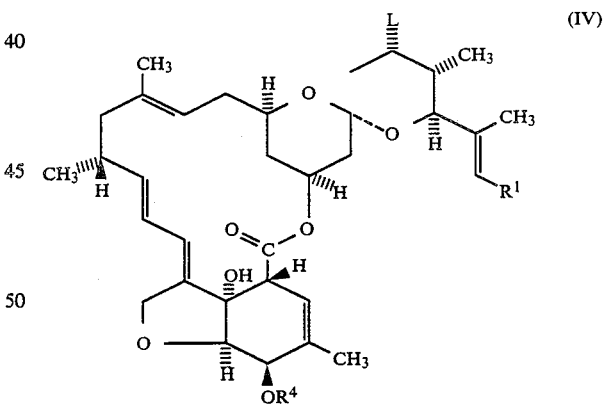

(IV)

[where $R^1$ and $-OR^4$ are as just defined and L is an atom or group removable by reduction, for example, by homolytic reduction such as the group $R^{11}OCSO-$ [where $R^{11}$ is $C_{1-6}$ alkyl, such as phenyl, or $(C_{1-6}$alkyl)aryl such as a p-tolyloxythiocarbonyloxy group]].

Suitable reagents which may be used to introduce the moiety L include, for example, aryl halothionoformales such as p-tolyl chlorothionoformate. The reaction may be carried out in the presence of a base, for example an amine such as pyridine in a solvent such as a halogenated hydrocarbon e.g. dichloromethane.

If desired the intermediate compounds of formula (IV) may be isolated.

Intermediates of formula (IV) may then be reduced to yield the desired compound of formula (II) using a reducing agent such as an alkyl tin hydride (e.g. tri-n-butyl tin hydride) in the presence of a radical initiator such as a peroxide, an azobisisobutyronitrile or light.

The reaction may conveniently be effected in a suitable solvent which may be selected from a ketone, e.g. acetone; an ether, e.g. dioxan, a hydrocarbon, e.g. hexane or toluene; a halogenated hydrocarbon e.g. trichlorobenzene; or an ester e.g. ethyl acetate. Combinations of such solvents either alone or with water may also be used.

The reaction may be carried out at a temperature of from 0°–200° C., preferably from 20°–130° C.

In a further process according to the invention a compound of formula (II) in which $R^2$ and $R^3$ together with the carbon atom to which they are attached represent $>C=O$ may be prepared by oxidising a compound of formula (III) wherein $OR^5$ is a hydroxyl group and $OR^4$ is a substituted hydroxyl group followed by deprotection of the group $OR^4$ is a where a compound in which $OR^4$ is a hydroxy group is required and, if desired, followed by resubstitution to give a compound of formula (II) in which $OR^4$ is a substituted hydroxyl group. The reaction may be effected with an oxidising agent serving to convert a secondary hydroxyl group to an oxo group whereby a compound of formula (II) is produced.

Suitable oxidising agents include quinones in the presence of water e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide: a dialkylsulphoxide e.g. dimethylsulphoxide, in the presence of an activating agent such as N,N'-dicyclohexylcarbodiimode or an acyl halide, e.g. oxalyl choride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used.

The reaction may be carried out at a temperature of from −80° C. to +50° C.

According to a further aspect of the invention we provide a process for the production of compounds of formula (II) wherein $R^2$ and $R^3$ together with the carbon atom to which they are attached are a $>C=O$ group and $OR^4$ is a hydroxyl or methoxy group which comprises the step of cultivating an organism of the genus Streptomyces capable of producing at least one of the compounds of the invention, and if desired isolating said compound therefrom and also if desired modifying the $OR^4$ group by methods such as described above.

The preferred microorganisms capable of producing the above substances are strains of a new species of the genus Streptomyces which has been named *Streptomyces thermoarchaensis*. A sample of this microorganism, which is a soil isolate, has been deposited (Sept. 10th, 1984) in the permanent culture collection of the National Collections of Industrial and Marine Bacteria, Torry Research Station, Aberdeen, United Kingdom, and has been assigned the Accession number NCIB 12015. Mutants of *Streptomyces thermoarchaensis* NCIB 12015 may also advantageously be used, and four mutant strains have been deposited (26th June 1985) in the permanent culture collection of the National Collections of Industrial and Marine Bacteria and have been assigned the Accession numbers NCIB 12111, NCIB 12112, NCIB 12113 and NCIB 12114.

The production of compounds of the invention by fermentation of a suitable Streptomyces organism may be effected by conventional means i.e. by culturing the Streptomyces organism in the presence of assimilable sources of carbon, nitrogen and mineral salts.

Assimilable sources of carbon, nitrogen and minerals may be provided by either simple or complex nutrients. Sources of carbon will generally include glucose, maltose, starch, glycerol, molasses, dextrin, lactose, sucrose, fructose, carboxylic acids, amino acids, glycerides, alcohols, alkanes and vegetable oils. Sources of carbon will generally comprise from 0.5 to 10% by weight of the fermentation medium.

Sources of nitrogen will generally include soya bean mean, corn steep liquors, distillers solubles, yeast extracts, cottonseed meal, peptones, ground nut mean, malt extract, molasses, casein, amino acid mixtures, ammonia (gas or solution), ammonium salts or nitrates. Urea and other amides may also be used. Sources of nitrogen will generally comprise from 0.1 to 10% by weight of the fermentation medium.

Nutrient minerals salts which may be incorporated into the culture medium include the generally used salts capable of yielding sodium, potassium, ammonium, iron, magnesium, zinc, nickel, cobalt manganese, vanadium, chromium, calcium, copper, molybdenum, boron, phosphate, sulphate, chloride and carbonate ions.

Cultivation of the Streptomyces organism will generally be effected at a temperature of from 20° to 50° C. preferably from 25° to 40° C., especially around 34° C. and will desirably take place with aeration and agitation e.g. by shaking or stirring. The medium may initially be inoculated with a small quantity of a sporulated suspension of the microorganism but in order to avoid a growth lag a vegetative inoculum of the organism may be prepared by inoculating a small quantity of the culture medium with the spore form of the organism, and the vegetative inoculum obtained may be transferred to the fermentation medium, or, more preferably to one or more seed stages where further growth takes place before transfer to the principal fermentation medium. The fermentation will generally be carried out in the pH range 5.5 to 8.5, preferably 5.5 to 7.5.

The fermentation may be carried out for a period of 2–10 days, e.g. about 5 days.

Where it is desired to separate material containing compounds according to the invention from the whole fermentation broth or to isolate any of the individual compounds this may be carried out by conventional isolation and separation techniques. The compounds according to the invention are predominantly contained in the mycelia of the cells, but may also be found in the fermentation broth and, therefore, the isolation techniques may also be applied to the fermentation broth after clarification. It will be appreciated that the choice of isolation techniques may be varied widely.

The compounds of the invention may be isolated and separated by a variety of fractionation techniques, for example adsorption-elution, precipitation, fractional crystallisation and solvent extraction which may be combined in various ways.

Solvent extraction and chromatography have been found to be most suitable for isolating and separating the compounds of the invention.

Following the fermentation the mycelia may be harvested using conventional techniques, For example, filtration or centrifugation. Thereafter, for example, the material may be extracted from the mycelia with an appropriate organic solvent such as a ketone. e.g. acetone, methylethyl ketone or methylisobutyl ketone; a hydrocarbon, e.g. hexane; a halogenated hydrocarbon e.g. chloroform, carbon tetrachloride or methylene chloride; an alcohol, e.g. methanol or ethanol; or an ester, e.g. methyl acetate or ethyl acetate. It will be appreciated that if the mycelia contain significant amounts of water, it will be preferable to use a water-soluble solvent.

Generally, more than one extraction is desirable to achieve optimum recovery. Preferably the first extraction is carried out using a water miscible solvent such as methanol or acetone. The antibiotics may be recovered as a crude extract by removal of the solvent. The solvent extracts may then themselves be extracted, if desired after reduction of the solvent volume, for example by evaporation. At this stage it is preferable to use a water-immiscible solvent such as hexane, chloroform, methylene chloride or ethyl acetate or mixtures thereof, sufficient water being added to achieve satisfactory partition of the antibiotic compounds. Removal of the water-immiscible phase yields a material containing one or more compounds of the invention, possibly together with Antibiotics S541 compounds.

Purification and/or separation of the compounds of the invention may be effected by conventional techniques such as for example, chromatography (including high performance liquid chromatography, 'hplc') on a suitable support such as silica, a non-functional macroreticular adsorption resin for example cross linked polystyrene resins such as Amberlite XAD-2, XAD-4 or XAD-1180 resins (Rohm & Haas Ltd), or an S112 resin (Kastell Ltd) or on an organic solvent-compatible cross-linked dextran such as Sephadex LH20 (Pharmacia UK Ltd), or, in the case of hplc, reverse phase supports such as hydrocarbon linked silica e.g. $C_{18}$-linked silica. The support may be in the form of a bed, or more preferably packed in a column. In the case of non-functional macrorelicular resins such as XAD-1180 or S112, mixtures of organic solvents such as acetonitrile with water may be used for elution.

A solution of the compounds in a suitable solvent will generally be loaded on to the silica or Sephadex columns if desired after first reducing the volume of solvent. The column may optionally be washed and then eluted with a solvent of suitable polarity. In the case of Sephadex and silica, alcohols, such as methanol; hydrocarbons, such as hexane; acetonitrile; halogenated hydrocarbons such as chloroform or methylene chloride; or esters such as ethyl acetate may be used as solvents. Combinations of such solvents either alone or with water may also be used.

Elution and separation/purification of the compounds of the invention may be monitored by conventional techniques such as thin layer chromatography and high performance liquid chromatography or by utilising the properties of the compounds described hereinafter.

The compounds according to the invention may initially be purified by chromatography over silica, preferably using an eluant such as chloroform:ethyl acetate, optionally followed by high performance liquid chromatography. The purified material produced may be then subjected to chromatography on a Sephadex column preferably using an eluant such as acetonitrile and compounds according to the invention may then be isolated using high performance liquid chromatography.

By a suitable combination of the foregoing procedures, the compounds of formula (II) as just defined have been isolated as solids in substantially pure form. It will be appreciated that the order in which the above purification steps are carried out, the choice of those which are used and the extent of purification achieved may be varied widely. The compounds may be used, however, as described above, at levels of purity appropriate to their intended use. For use in human medicine, purities of at least 90%, preferably greater than 95% are desirable, for veterinary or other use, lower purities will suffice, for example 50% or lower.

The intermediate Antibiotics S541 compounds of formula (III) in which $OR^5$ is a hydroxy group and $OR^4$ is a hydroxy or methoxy group may also be obtained using the fermentation and isolation methods described above for example as described in South African Patent No. 85/7049. Other intermediates of formula (III) may be prepared from these compounds using methods described above for the preparation of compounds of formula (II).

Salts of acids of formula (II) may be prepared by conventional methods, for example by treating the acid with a base or converting one salt into another by exchange of ion. The invention is further illustrated by the following Preparations and Examples. All temperatures are in °C.

Compounds are named by reference to parent "Factors" which are the compounds listed below with the formula (V)

| Factor | R | $R^1$ |
|---|---|---|
| A | —H | —CH(CH$_3$)$_2$ |
| B | —CH$_3$ | —CH$_3$ |
| C | —H | —CH$_3$ |
| D | —H | —CH$_2$CH$_3$ |
| E | —CH$_3$ | —CH$_2$—CH$_3$ |
| F | —CH$_3$ | —CH(CH$_3$)$_2$ |

Factors A, B, C, D, E and F may be prepared as described in South African Patent No. 85/7049.

EXAMPLE 1

5-Phenoxyacetoxy and 5,23-Diphenoxyacetoxy Factor A

Factor A (2.0 g) in dichloromethane (25 ml) and pyridine (0.35 ml) at 0° was treated with a solution of phenoxyacetyl chloride (0.5 ml) in dichloromethane. After 18 hr at 3° the solution was treated with pyridine (1.0 ml) and with phenoxyacetyl chloride (1.0 ml) in dichloromethane (5 ml). The solution was stirred at 0° to 5° for 30 min before being poured into ice-water. Ether (100 ml) was added and the mixture stirred for 20 min. The aqueous layer was extracted with ether. The ether layers were combined, washed successively with water and brine, dried and evaporated. The residue was purified by silica chromatography using dichloromethane:acetone (40:1) to give the title compounds as a mixture (1.8 g, monoacyl:diacyl=6:1), which was separated by reverse-phase preparative hplc to give 5-phenoxyacetoxy Factor A, δ (CDCl$_3$) include 6.8 to 7.4 (m; 5H) and 4.66 (s; 2H), m/z include 746, 728, 710, 594 and 576, and 5,23-diphenoxyacetoxy Factor A, δ (CDCl$_3$) include 6.8 to 7.4 (m, 10H), 4.60 (s, 2H) and 4.70 (s, 2H).

EXAMPLE 2

5-Phenoxyacetoxy-23-(4-methylphenoxythionocarbonyloxy) Factor A

5-Phenoxyacetoxy Factor A (747 mg) in dichloromethane (10 ml) at 0° under nitrogen was treated with pyridine (0.81 ml) and then with 4-methylphenyl chlorothionoformate (0.75 g) in dichloromethane (2 ml). The dark solution was stirred for 15 min at 0° and then for 22 hr without cooling. The mixture was poured into cold water and brine, and extracted with ether. The combined ether layers were washed with water and brine, dried and evaporated. The residue was purified by silica column chromatography and reverse-phase preparative hplc to give the title compound (430 mg), δ (CDCl$_3$) include 3.34 (m; 1H), 3.58 (m; 1H), 3.97 (d10; 1H), 4.72 (s; 2H), 5.4 (m; 1H), 5.59 (d6; 1H) and 6.9 to 7.4 (m; 9H), m/z include 728, 616, 576, 466, 464, 448, 354, 297, 247, 219 and 151.

EXAMPLE 3

5-Tert-butyldimethylsilyloxyacetoxy Factor A

Factor A (2.144 g) in anhydrous ether (25 ml) and pyridine (2.5 ml) at 0° under nitrogen was treated dropwise with t-butyldimethylsilyloxyacetyl chloride (1.2 g) in ether (10 ml). The mixture was stirred for 90 min at 0° before being treated dropwise with more acid chloride (1.10 g) in ether (10 ml). The mixture was stirred at 0° for 60 min and poured into cold water and ether. The aqueous layer was washed with ether. The combined organic layers were washed with water and brine, dried, and evaporated. The residue was purified by silica chromatography using dichloromethane:acetone (25:1) as eluent to give the title compound, δ (CDCl$_3$) include 0.09 (s; 6H), 0.78 (d6; 3H), 0.90 (s; 9H), 0.93 (d6; 3H), 0.97 (d6; 3H), 1.03 (d6; 3H), 1.51 (s; 3H), 1.59 (s; 3H), 1.74 (s; 3H), 3.32 (m; 1H), 3.52 (d10; 1H), 3.64 (m; 1H), 3.74 (d10; 1H), 3.82 (m; 1H), 4.32 (s; 2H) and 5.57 (d5; 1H), m/z include 784, 766, 748, 595, 577, 484, 466, 354, 314, 297, 265, 247, 237, 219 and 151.

EXAMPLE 4

5-Trimethylsilyloxy Factor A

A solution of Factor A (250 mg) in dry tetrahydrofuran (10 ml) was treated with dry triethylamine (0.12 ml) and trimethylsilyl chloride (0.11 ml). The mixture was stirred for 1 hr at 20°, and poured into ether and water. The organic layer was washed with water, dried and evaporated. The residue was purified by preparative tlc using dichloromethane:acetone (10:1) as eluent to give the title compound, δ (CDCl$_3$) include 0.18 (s; 6H), 0.08 (d6; 3H), 0.96 (d6; 3H), 1.00 (d6; 3H), 1.06 (d6; 3H), 1.53 (s; 3H), 1.60 (s; 3H), 1.78 (s; 3H), 3.33 (m; 1H), 3.75 (d10; 1H), and 4.41 (d6; 1H), m/z include 684, 666, 651, 633, 484, 466, 448, 354, 314, 297, 265, 248, 247, 237, 219 and 151.

EXAMPLE 6

5-Tert-butyldimethylsilyloxy Factor A

Factor A (250 mg) and imidazole (163 mg) in dry dimethylformamide (10 ml) were treated with t-butyldimethylsilyl chloride (197 mg). The solution was stirred for 2 hr and poured into cold water. The mixture was thoroughly extracted with ether, and the combined ether extracts were dried and evaporated. The residue was purified by silica chromatography, using dichloromethane:acetone (10:1) as eluent to give the title compound (235 mg), δ (CDCl$_3$) include 0.13 (s; 6H), 0.80 (d6; 3H), 0.92 (s, 9H), 0.96 (d6; 3H), 1.00 (d6; 3H), 1.03 (d6; 3H), 1.53 (s; 3H), 1.60 (s; 3H); 1.80 (s; 3H), 3.37 (m; 1H), 3.56 (d10; 1H), 3.64 (m; 1H), 3.75 (d10, 1H) and 4.43 (d5; 1H), m/z include 726, 708, 691, 651, 633, 466, 448, 354, 314, 297, 265, 247, 219 and 151.

EXAMPLE 7

5-Acetoxy and 5,23-Diacetoxy Factor A

Factor A (3.0 g) in pyridine (20 ml) at −5° was treated with acetic anhydride (8 ml) and the resulting solution left at 3° for 20 hr. Benzene (100 ml) was added and the solution concentrated in vacuo. The residual oil was chromatographed over silica using dichloromethane:acetone (40:1) as eluent to give the 5-acetate of Factor A (2.06 g), containing the 5,23-diacetate (10%). The compounds were separated by reverse-phase preparative hplc to give 5-acetoxy Factor A (79% recovery), $\lambda_{max}$ (EtOH) 244.5 nm ($E_1^1$ 462), δ (CDCl$_3$) includes 2.14 (s; 3H), m/z includes 654, 594 and 576, and 5,23-diacetoxy Factor A (6.5% recovery), δ (CDCl$_3$) include 2.01 (s; 3H) and 2.13 (s; 3H), m/z include 696 and 636.

EXAMPLE 8

5,23-Diacetoxy Factor A

A solution of Factor A (600 mg) in dry pyridine (1.0 ml) was treated with excess acetic anhydride (0.50 ml) and a few crystals of 4-N,N-dimethylaminopyridine. After 24 h. at room-temperature the mixture was poured into ether and the organic phase then washed successively with 2N hydrochloric acid, saturated aqueous sodium bicarbonate solution, and finally brine. Evaporation of the dried organic phase provided a gum which was purified by chromatography over Merck Kieselgel 60, 230–400 mesh silica (45 g). Elution of the column with dichloromethane:ether (9:1) afforded the title compound as a colourless foam (560 mg), $[\alpha]_D^{26}$+169° (c 0.48, CHCl$_3$).

The compounds of Examples 9 and 10 were prepared in a similar manner except where indicated:

EXAMPLE 9

23-Acetoxy Factor B m.p. 256°–258° (dec.), $[\alpha]_D^{22}+175°$ (c 0.40, CHCl$_3$), $\lambda_{max}^{EtOH}$ 238.5 (26,200) and 244.5 nm ($\lambda_{max}$ 28,850); $\epsilon_{max}$(CHBr$_3$) 3460 (OH) and 1708 cm$^{-1}$ (ester), δ(CDCl$_3$) include 5.48 (q 7Hz, 1H), 4.90 (m, 1H), 3.99 (d 5 Hz, 1H), 3.55 (m, 1H), 3.49 (s, 3H), 3.29 (m,1H), 2.00 (s, 3H), 1.79 (s, 3H), 1.66 (d 6 Hz, 3H), 1.58 (s, 3H), 1.52 (s, 3H), 0.98 (d 7 Hz, 3H), and 0.71 (d 7 Hz, 3H). m/z=640 (M+). from Factor B (392 mg). The gum obtained after the ether extraction was crystallised from petroleum spirit (60°–80°) and recrystallised from diisopropyl ether to give the title compound as needles.

EXAMPLE 10

5,23-Diacetoxy Factor C m.p. 211°–213°, $[\alpha]_D^{22}+200°$ (c 0.40, CHCl$_3$), $\lambda_{max}^{EtOH}$ 238.5 (30,400) and 245 nm ($\lambda_{max}$ 32,500); $\epsilon_{max}$ 3440 (OH) and 1718 cm$^{-1}$ (acetoxy and ester); δ (CDCl$_3$) include 4.90 (m, 1H), 4.04 (d 6 Hz, 1H), 3.96 (d 10 Hz, 1H), 3.58 (m, 1H), 3.32 (m, 1H), 2.14 (s, 3H), 1.75 (s, 3H), 1.67 (d 6 Hz, 3H), 1.60 (s, 3H), 1.52 (s, 3H), 0.99 (d 6 Hz, 3H), and 0.71 (d 7 Hz, 3H). m/z=668 (M+), from Factor C (312 mg). The reaction mixture was poured into ethyl acetate rather than ether and finally crystallised on trituration with diisopropyl ether.

EXAMPLE 11

23-Acetoxy Factor A

To a stirred and cooled (0°–5°) solution of the compound of Example 8 (530 mg) in methanol (10 ml) was added dropwise an aqueous solution (1 ml) of sodium hydroxide (30 mg). After 1.3 h the mixture was poured into ethyl acetate and the organic phase then washed successively with 2N. hydrochloric acid, water, and finally brine. Evaporation of the dried organic phase gave a yellow gum which in dichloromethane was introduced on to a column of Merck Kieselgel 60, 230–400 mesh silica (50 g) made up in the same solvent. Elution with dichloromethane:ether (9:1) provided the title compound which was obtained as an almost colourless solid by evaporation of an n-pentane solution. This material (330 mg) had $[\alpha]_D^{23}+166°$ (c 0.64, CHCl$_3$), $\lambda_{max}^{EtOH}$ 239 (26,500) and 245 nm ($\lambda_{max}$ 29,300); $\lambda_{max}$(CHBr$_3$) 3540, 3460 (OH) and 1712 cm$^{-1}$ (ester); δ(CDCl$_3$) include 4.89 (m, 1H), 4.27 (t 6 Hz, 1H), 3.93 (d 6 Hz, 1H), 3.91 (d 10 Hz, 1H), 3.55 (m, 1H), 3.25 (m, 1H) 2.01 (s,3H), 1.85 (s, 3H), 1.59 (s, 3H), 1.51 (s, 3H) 1.03 (d 6 Hz, 3H), 0.98 (d 6 Hz, 3H), 0.94 (d 6 Hz, 3H), and 0.69 (d 7 Hz, 3H). m/z=654 (M+). The compounds of Examples 12–14 were prepared in a similar manner:

EXAMPLE 12

23-Keto Factor C $[\alpha]_D^{22}+110°$ (c 0.40, CHCl$_3$); $\lambda_{max}^{EtOH}$ 245 nm ($\epsilon_{max}$ 28,500); $\nu_{max}$ (CHBr$_3$) 3540, 3470 (OH) and 1710 cm$^{-1}$ (ester and ketone). δ(CDCl$_3$) include 5.47 (d-ql and 6 Hz, 1H), 4.28 (t-6 Hz, 1H), 3.94 (d 6 Hz, 1H), 3.74 (d 11 Hz, 1H), 3.50 (m, 1H), 3.37 (m, 1H), 1.87 (s, 3H), 1.69 (d 6 Hz, 3H), 1.50 (s, 3H), 0.99 (d 6 Hz, 3H), and 0.85 (d 7 Hz, 3H). m/z=582 (M+), from the compound of Example 20 (120 mg)

EXAMPLE 13

23-Deoxy Factor C (80 mg)

$[\alpha]_D^{23}+104°$ (c 0.56, CHCl$_3$); $\lambda_{max}^{EtOH}$ 244.5 nm ($\epsilon_{max}$ 28,050); $\nu_{max}$ (CHBr$_3$) 3540, 3450 (OH), 1702 cm$^{-1}$ (ester). δ (CDCl$_3$) include 4.28 (t 6 Hz, 1H), 3.95 (d 6 Hz, 1H), 3.57 (m, 1H), 3.45 (d 10 Hz, 1H), 3.26 (m, 1H) 1.87 (s, 3H), 1.65 (d 7 Hz, 3H), 1.59 (s, 3H), 1.53 (s, 3H), 0.99 (d 6 Hz, 3H), and 0.69 (poorly defined doublet. 5 Hz, 3H). m/z=568 (M+), from the compound of Example 26 (125 mg) as a colourless foam.

EXAMPLE 14

23-Acetoxy Factor C $[\alpha]_D^{23}+139°$ (c 0.52, CH$_2$Cl$_2$); $\lambda_{max}^{EtOH}$ 244.5 nm ($\delta_{max}$ 29,400); $\nu_{max}$(CHBr$_3$) 3550, 3480 (OH); 1716 (ester and acetate) and 1255 cm$^{-1}$ (acetate); δ(CDCl$_3$) include 4.91 (q, 3 Hz, 1H); 2.03 (s, 3H) and 1.64 (d, 7 Hz, 3H) and 1.60 (s, 3H); m/z=626 (M+), from the compound of Example 10 as a white amorphous solid.

EXAMPLE 15

23-p-Tolyloxythiocarbonyloxy Factor B

Factor B (600 mg) was dissolved in dry dichloromethane (5 ml) and to this solution was added dry pyridine (800 mg) and p-tolylchlorothionoformate (750 mg). After 24 h. at ambient temperature the mixture was poured into ether and the organic solution worked up for neutral material. The crude thiocarbonate in dichloromethane was loaded-on to a column of silica (50 g) made up in the same solvent. Elution of the column with dichloromethane:ether (95:5) provided a major component which was purified further by preparative reverse-phase HPLC. The title compound was isolated as a colourless foam (417 mg), $[\alpha]_D^{23}+160°$ (c 0.40, CHCl$_3$), $\lambda_{max}^{EtOH}$ 238 nm ($\epsilon_{max}$ 35,900), $\nu_{max}$ (CHBr$_3$) 3470, 3530 (OH), 1705 (ester); δ (CDCl$_3$) include 7.18 (d 9 Hz, 2H), 6.98 (d, 9 Hz, 2H), 5.49 (q 6 Hz, 1H), 4.02 (d 5 Hz, 1H), 3.58 (m, 1H), 3.31 (m, 1H), 3.49 (s,3H), 2.36 (s,3H), 1.81 (s, 3H), 1.68 (d 6, 3H), 1.61 (s,3H), 1.53 (s, 3H), 1.00 (d 6 Hz 3H), and 0.82 (d 7 Hz, 3H). m/z=748 (M+).

The compound of Example 16 was prepared in a similar manner:

EXAMPLE 16

5-Acetoxy,23-p-tolyloxythiocarbonyloxy Factor C (430 mg), $[\alpha]_D^{23}+133°$ (c 0.48, CHCl$_3$); $\lambda_{max}^{EtOH}$ 237.5 (36,900), 244 (36,900) and 273 nm ($\nu_{max}$ 2,400); $\nu_{max}$(CHBr$_3$) 3500 (OH), 1732 (acetate) and 1710 cm$^{-1}$ (ester). δ (CDCl$_3$) include 7.17 (d 8 Hz, 2H), 6.99 (d 8 Hz, 2H), 4.04 (d 6 Hz, 1H), 3.98 (d 10 Hz,1H), 3.57 (m, 1H), 3.31 (m, 1H), 2.34 (s, 3H), 2.14 (s, 3H), 1.74 (s, 3H), 1.66 (d 6 Hz, 3H), 1.60 (s, 3H), 1.52 (s, 3H), 0.99 (d 6 Hz, 3H), and 0.81 (d 7 Hz, 3H). m/z=776 (M+), From the compound of Example 17 (500 mg) as a colourless foam.

EXAMPLE 17

5-Acetoxy Factor C

To a solution of Factor C (338 mg) in dry pyridine (0.5 ml) was added acetic anhydride (71 mg). After 20 h. at room-temperature the mixture was poured into dichloromethane and the solution worked up for neutral material. The crude material so obtained was purified by chromatography over Merck K 60, 230–400 mesh silica (28 g.). Elution of the column with dichloromethane:ether (9:1) gave the title compound (210 mg) which was recovered as a crystalline solid m.p ca. 135°, $[\alpha]_D^{23} +142°$ (c 0.64, CHCl$_3$); $\lambda_{max}^{EtOH}$ 244.5 nm ($\epsilon_{max}$ 31,250); $\nu_{max}$ (CHBr$_3$) 3490 (OH), 1718 (ester) and 1730 (acetoxy); $\delta$ (CDCl$_3$) include 4.03 (d 6 Hz,1H), 3.79 (d 10 Hz, 1H), 3.54 (d 10 Hz, 1H), 3.31 (m, 1H), 2.14 (s, 3H), 1.74 (s, 3H), 1.66 (d 7 Hz, 3H), 1.60 (s, 3H), 1.52 (s, 3H), 0.98 (d, 6 Hz, 3H) and 0.78 (d 7 Hz, 3H). m/z=626 (M+).

EXAMPLE 18

5-Acetoxy-23-keto Factor A

A solution of oxalyl chloride (1.96 ml) in dry dichloromethane (25 ml) at −70° under nitrogen was treated dropwise with a solution of dimethylsulphoxide (3.19 ml) in dry dichloromethane (15 ml) and then dropwise with a solution of 5-acetoxy Factor A (4.91 g) in dry dichloromethane (30 ml). The resulting solution was stirred at −70° for 1.5 hr before being treated dropwise with a solution of triethylamine (12.6 ml) in dry dichloromethane (40 ml). The reaction mixture was stirred for 1.25 hr without cooling and poured into a (1:1) mixture of cold water and ether. The aqueous layer was extracted with ether. The combined organic layers were washed with water, brine, dried and evaporated. The residual foam was chromatographed over silica using dichloromethane:acetone (50:1) to give the title compound (3.4 g), $\delta$ (CDCl$_3$) include 3.33 (m; 1H), 3.49 (m; 1H), 3.70 (d10; 1H) and 5.52 (d5; 1H), m/z include 652, 634, 609, 591, 574, 482, 263, 235 and 151.

The compound of examples 19 and 20 were prepared in a similar manner.

EXAMPLE 19

23-Keto Factor B (160 mg)

m.p. 213°–215° (softening ca 209°), $[\alpha]_D^{22} +122°$ (c 0.36, CHCl$_3$; $\lambda_{max}^{EtOH}$ 238.5 (26,400), 244.5 (28,700) and 282 nm ($\epsilon_{max}$ 400); $\nu_{max}$ (CHBr$_3$) 3450 (OH) and 1710 cm$^{-1}$ (ester and ketone); $\delta$ (CDCl$_3$) include 5.47 (q 6 Hz, 1H), 4.02 (d 6 Hz, 1H), 3.95 (d 6 Hz; 1H), 3.73 (d 10 Hz, 1H), 3.51 (s, 3H), 3.31 (m, 1H), 1.81 (s, 3H), 1.69 (s, 3H), 1.67 (d 6 Hz, 3H), 1.50 (s, 3H), 0.97 (d 6 Hz, 3H) and 0.82 (d 7 Hz, 3H). m/z=596 (M+), from Factor B (599 mg) as a microcrystalline solid upon crystallisation from ether.

EXAMPLE 20

5-Acetoxy, 23-keto Factor C (290 mg)

m.p. 241°–243°, $[\alpha]_D^{23} +118°$ (c 0.60, CHCl$_3$); $\lambda_{max}^{EtOH}$ 245 nm ($\epsilon_{max}$ 30,900); $\nu_{max}$ (CHBr$_3$) 3460 (OH), 1712 cm$^{-1}$ (ester and ketone). $\delta$ (CDCl$_3$) include 4.05 (d 6 Hz, 1H), 3.75 (d 10 Hz, 1H), 3.52 (m, 1H), 3.33 (m, 1H), 2.14 (s, 3H), 1.76 (s, 3H), 1.69 (s, 3H), 1.68 (d 5 Hz, 3H), 1.51 (s, 3H), 0.98 (d 6 Hz, 3H), and 0.85 (d 7 Hz, 3H). m/z=624 (M+), From the compound of Example 17 as microcrystalline needles upon crystallisation from diisopropylether/ether.

EXAMPLE 21

23-Keto Factor A

The compound of Example 18 (276 mg) in methanol (5 ml) at 0° was treated dropwise with a solution of 2N-sodium hydroxide (0.42 ml) in methanol (1.0 ml). The solution was left at 5° for 5 hr before being poured into cold water. The mixture was extracted with ether and ethyl acetate. The combined organic layers were washed with brine, dried, and evaporated to leave a solid, which was purified by preparative tlc using dichloromethane:acetone (10:1) as solvent to give the title compound (140 mg), $\delta$ (CDCl$_3$) include 3.28 (m; 1H), 3.48 (m; 1H), 3.70 (d10; 1H) and 4.28 (tr7; 1H), m/z include 592, 549, 482, 370, 263, 235 and 151.

EXAMPLE 22

5-Tert-butyldimethylsilyloxyacetoxy-23-keto Factor A

The compound of Example 3 (300 mg) in dry dimethylformamide (5 ml) at 22° was treated with pyridinium dichromate (PDC) (1.40 g) and stirred for 3.5 hr. More PDC (1.0 g) was added and the stirring continued for 1 hr. The mixture was poured into ice-water and ether. The aqueous layer was washed thoroughly with ether. The combined organic layers were washed with water and brine, dried and evaporated. The residue was purified by preparative silica tlc, using dichloromethane:acetone (40:1) as eluent, to give a solid (150 mg), which was shown by ms/hplc to contain the title compound, m/z include 782, 592, 549, 370, 340, 263, 235 and 151.

EXAMPLE 23

23-Keto Factor A 0.4 ml of a spore suspension of *Streptomyces thermoarchaensis* NCIB 12015 in 10% glycerol was used to inoculate a 250 ml Erlenmyer flask containing 50 ml medium as:

|  | gL$^{-1}$ |
| --- | --- |
| D-glucose | 15.0 |
| Glycerol | 15.0 |
| Soya Peptone | 15.0 |
| NaCl | 3.0 |
| CaCO$_3$ | 1.0 |

Distilled water to 1 liter. pH was adjusted to 7.0 with aqueous NaOH before autoclaving.

The flask was incubated at 28° for 2 days on a rotary shaker operating at 250 rpm with a 50 mm diameter orbital motion. 4 ml portions liter liter were then used to inoculate each of four 2 liter flat-bottomed flasks each containing 200 mls of the same medium, before incubation under the same conditions for 2 days.

The contents of the 4 flasks were then used to inoculate a 70 liter fermenter vessel containing 40 liters of the same medium supplemented with polypropylene glycol 2000 (0.06%). Polypropylene glycol 2000 was added as required throughout the fermentation to control foaming. The fermentation was carried out at 28°, with agitation and aeration sufficient to maintain a dissolved oxygen level of greater than 30% of saturation. After 24 hours of fermentation, 800 and 9 liter portions were transferred to a 70 liter fermenter containing 40 liters of medium, and a 700 liter fermenter containing 450 liters of medium, respectively. Both these fermenters contained the following medium:

|  | gL$^{-1}$ |
| --- | --- |
| D-Glucose | 2.5 |
| Malt Dextrin (MD30E) | 25.0 |
| Arkasoy 50 | 12.5 |
| Beet Molasses | 1.5 |
| K$_2$HPO$_4$ | 0.125 |
| CaCO$_3$ (Ar) | 1.25 |
| Silicone 1520 (Dow Corning) | 0.6 |

Distilled water to 1 liter. pH was adjusted to 6.5 with aqueous H₂SO₄ before sterilisation.

These fermentations were carried out at 34° with agitation and aeration sufficient to maintain a dissolved oxygen level of greater than 30% of saturation. Polypropylene glycol 2000 antifoam was added as required. After 24 hours, the pH in each fermenter was controlled to 7.2 with the addition of aqueous H₂SO₄. The fermentations were harvested and bulked after 4 days.

The mycelium (10.4 kg) from the bulked harvest broth (423 L) was collected in a Sharples PS16AY centrifuge. The mycelium was stirred vigorously in methanol (50 L) for 40 min and then filtered. The residue was resuspended in methanol (15 L) and again filtered. The combined filtrates (55 L) were then mixed with water (27 L) and 60–80 petroleum ether (30 L) and stirred for 20 min.

The phases were separated in a Westfalia MEM1256 centrifuge, and the methanol phase (75 L) was mixed with more water (38 L) and 60–80 petroleum ether (30 L). After 20 min the phases were again separated in the centrifuge, acetone (2 L) being added to the petroleum ether phase to break the emulsion. The methanol phase (110 L) was mixed with water (38 L) and 60–80 petroleum ether (30 L) for a third time, the phases being separated as before. Acetone (3 L) was again added to the petroleum ether phase to break the emulsion.

The three hexane phases were bulked (90 L) and concentrated at low pressure (vapour temperature 25°). The concentrate (9.8L) was dried with sodium sulphate (3Kg) and then evaporated to an oil.

The oil was dissolved in dichloromethane (0.5 L) and filtered through Dicalite 478. The solution (0.9 L) was loaded onto a column (150×10 cm) silica (Merck) at 6L/h, washed with dichloromethane (4L) and eluted with a mixture of chloroform; ethylacetate (3:1 $v_v$). The fraction eluting between 14.6 and 33.3 L was concentrated to a solid and redissolved in chloroform:ethyl acetate (13:1 $v_v$).

The solution was rechromatographed on a column of silica with the same solvent. The fraction eluting between 14.5 and 31.5 L was dried to a solid and dissolved in chloroform:ethylacetate (3:1 $v_v$). This solution was again chromatographed on silica under the same conditions as before and the fraction eluting between 14 and 31 L was dried to a solid.

The solid was dissolved in 70% $v_v$ acetonitrile in water (1.23 L) with enough methanol added to give a clear solution. The solution was chromatographed in 5 ml portions on a column of Spherisorb ODS2. The column was eluted with 70% acetonitriie at a flow rate which increased from 20 mL/min to 34 mL/min over 21 min. The fraction from each portion which eluted between 12.4 and 16 were collected together and diluted with an equal volume of water. This solution was then loaded onto a column of Montedison S112 macroreticular polystyrene (2 L). The column was washed with 35% acetonitrile and eluted with acetone. The fraction eluting between 0.5 and 1.25 L was dried to a solid.

The solid was dissolved in acetonitrile (20 mL) and chromatographed on a column of Sephadex LH20 in the same solvent. The fractions eluting between 1.08 and 1.26 L were collected and dried to a solid.

The solid was dissolved in 60% acetonitrile (10 mL) with enough methanol added to give a clear solution. It was chromatographed in 2 mL portions again on the column of Spherisorb ODS2 and eluted with 60% acetonitrile at 25 mL/min. The Fractions eluting between 0.95 L and 1.08 L were collected together and dried to a solid. This solid was redissolved in chloroform (5 mL) and chromatographed on a column of Merck silica gel 60. It was eluted with chloroform at 10 mL/min, and the fraction eluting between 400 mL and 790 mL was dried to give the title compound (33 mg) as a solid. The nmr spectrum was consistent with containing 23-keto Factor A.

E.I. mass spectroscopy yielded a molecular ion at 610 and gave characteristic fragments at 592
549
498
482
370
263
151

A sample was shown to contain 23-keto Factor A on hplc by comparison with authentic ketone produced by the chemical oxidation of Factor A.

EXAMPLE 24

5-Phenoxyacetoxy-23-deoxy Factor A

The compound of Example 2 (350 mg) and azobisisobutyronitrile (25 mg) in dry toluene (20 min) under nitrogen at 120° were treated dropwise with a solution of tri-n-butyltin hydride (0.5 ml) in dry toluene (10 ml). The solution was refluxed for 90 min, cooled and evaporated. The residue was chromatographed over silica, using dichloromethane:acetone (40:1) as solvent, to give the title compound (280 mg), δ (CDCl₃) include 3.32 (m; 1H), 3.42 (d10; 1H), 3.57 (m; 1H), 4.71 (s; 2H), 5.59 (d6; 1H) and 6.8 to 7.4 (m; 5H), m/z include 730, 712, 578, 560, 468, 450, 356, 314, 299, 249, 248, 221 and 151.

The compounds of Examples 25 and 26 were prepared in a similar manner.

EXAMPLE 25

23-Deoxy Factor B m.p. 184°–186°, $[\alpha]_D^{22}+158°$ (c 0.40, CHCl₃), $\lambda_{max}^{EtOH}$238.5 (28,150) and 244.5 nm ($\epsilon_{max}$30,650); $\nu_{max}$(CHBr₃) 3450 (OH) and 1705 cm⁻¹ (ester). δ (CDCl₃) include 4.01 (d 6 Hz, 1H), 3.95 (d 6 Hz, 1H), 3.49 (s, 3H), 3.29 (m, 1H), 1.80 (s, 3H), 1.64 (d 6 Hz, 3H), 1.58 (s, 3H), 1.53 (s, 3H), 0.98 (d 7 Hz, 3H), and 0.69 (d 6 Hz, 3H). m/z=582 (M+), from the compound of Example 15 (350 mg) except that the residue was chromatographed using dichloromethane followed by dichloromethane:ether (95:5) to give the title compound as a crystalline solid upon trituration with n-pentane.

EXAMPLE 26

5-Acetoxy, 23-deoxy Factor C (256 mg) m.p. 230° (dec.), $[\alpha]_D^{23}+147°$ (c 0.32, CHCl₃); $\lambda_{max}^{EtOH}$ 238.5 (28,000), 244.5 nm ($\epsilon_{max}$ 30,300); $\nu_{max}$ (CHBr₃) 3440 (OH), 1730 (acetoxy) and 1710 cm⁻¹ (ester). δ(CDCl₃) include 4.05 (d 5 Hz, 1H), 3.57 (m, 1H), 3.33 (m 1H), 2.15 (s, 3H), 1.75 (s, 3H), 1.64 (d 6 Hz, 3H), 1.59 (s, 3H), 1.53 (s, 3H), 0.99 (d 6 Hz, 3H) and 0.68 (d 5 Hz, 3H). m/z=610 (M+), From the compound of Example 16 (385 mg) upon crystallisation from n-pentane.

EXAMPLE 27

23-Deoxy Factor A

The compound of Example 24 (240 mg) was added to a saturated solution of ammonia in methanol (10 ml) at −5°. The solution was stirred at 0° to 10° for 2 hr before being evaporated to dryness. The residue was chromatographed over silica using dichloromethane:acetone (20:1) to give the title compound (180 mg), δ (CDCl$_3$) include 3.27 (m; 1H), 3.42 (d9; 1H), 3.54 (m; 1H), and 4.29 (t6; 1H), m/z include 596, 578, 560, 468, 450, 356, 314, 299, 249, 248, 221 and 151.

EXAMPLE 28

5-Acetoxy 23-mesyloxy Factor A

A solution of 5-acetoxy Factor A (46 g) in pyridine (30 ml) was cooled in an ice bath and was treated with methanesulphonic anhydride (2.2 g). After 30 minutes the mixture was allowed to warm to ambient temperature and after a further 60 minutes was partitioned between ethyl acetate and 2N hydrochloric acid. The organic phase was separated and was washed successively with 2N hydrochloric acid, with saturated aqueous sodium bicarbonate solution, and finally with saturated brine. The organic solution was dried (Na$_2$SO$_4$) and the solvent was evaporated to leave a foam which was chromatographed over a column of silica (Merck Art 9385) made up in hexane (60°–80°)/ethyl acetate (3:1) and eluted with the same solvent. Appropriate fractions of the major component were combined and the solvent was evaporated to give the title compound as a foam (2.08 g). $[\alpha]_D^{22}+154°$ (c=0.56; CHCl$_3$), $\lambda_{max}^{CHCl_3}$247 nm (ε29070); $\nu_{max}$ (CHBr$_3$) 3550, 3470 (OH) and 1735, 1715 (ester); δ(CDCl$_3$) include 4.90 (m, 1H), 3.05 (s, 3H) and 2.16 (s, 3H). EXAMPLE 29

23-Tosyloxy Factor B

Factor B (250 mg), tosic anhydride (204 mg) and a few crystals of 4-N,N-dimethylaminopyridine were stirred together in dry pyridine (0.5 ml) for 24 h. The mixture was poured into ether and the organic phase then washed successively with 2M hydrochloric acid, saturated aqueous sodium bicarbonate and finally brine. Evaporation of the dried (Na$_2$SO$_4$) ethereal layer gave crude material which in dichloromethane was introduced on to a column of silica gel (50 g, Merck Kieselgel 60, 203–400 mesh) made up in the same solvent. Elution with dichloromethane:ether (9:1) provided the major component which was purified further by preparative HPLC. The title compound was obtained as a gum $[\alpha]_D^{23}+173°$ (c 0.84, CHCl$_3$); $\lambda_{max}$ (EtOH 235 (30,000) and 244.5 nm ($\epsilon_{max}$ 30,800); $\nu_{max}$ (Cand 1708 cm$^{-1}$ (ester); δ (CDCl$_3$) includes 7.82 (d, 10 Hz, 2H), 7.29 (d, 10 Hz, 2H), 4.83 (q, 3 Hz, 1H), 3.50 (s, 3H) and 2.43 (s, 3H); m/z=752 (M+).

EXAMPLE 30

(a) 5-Acetoxy-23-n-butoxy Factor A

Silver carbonate (1 g) was added to a solution of 5-acetoxy Factor A (325 mg) in dry ether followed by iodobutane (0.5 ml) and silver perchlorate (550 mg). The mixture was stirred at room temperature for 20 h when collidine (0.5 ml) was added. After stirring for a further 20 min the mixture was filtered and the filtrate was washed successively with 2N hydrochloric acid, saturated aqueous sodium bicarbonate solution, and water. The dried organic phase was evaporated to near dryness and the oil was purified by chromatography over Merck Keiselgel 60 230–400 mesh. Elution of the column with hexane:ethyl acetate (3:1) afforded the title compound as a colourless foam (276 mg) $[\alpha]_D^{22}+160°$ (c 0.94, CHCl$_3$) $\lambda_{max}$ (EtOH) 245 nm ($\epsilon_{max}$ 28300); δ (CDCl$_3$) include 3.16 (m, 1H), 3.43 (m, 1H), 3.43 (m, 1H), 3.59 (m, 1H).

The following compound was prepared in a similar manner:

(b) 5-Acetoxy-23-ethoxy Factor A from 5-acetoxy Factor A and ethyl iodide. The title compound was afforded as a colourless foam $[\alpha]_D^{22}+167°$ (c 1.02, CHCl$_3$), $\lambda_{max}$(EtOH) 245 nm (ε, 28070), δ(CDCl$_3$) include 3.25 (m,1H), 3.46 (m, 1H), 3.64 (m,1H).

EXAMPLE 32

23-Methoxy Factor B

Silver salicyate (509 mg) was added to a solution of Factor B (128 mg) and methyl iodide (0.5 ml) in dry ether (50 ml) and the mixture was stirred for 4 days at room temperature, then filtered. The filtrate was evaporated and the resultant gum was purified by chromatography over Merck Keiselgel 60, 230–400 mesh (100 ml). Elution of the column with petroleum ether (b.p. 40°–60°):ethyl acetate (3:1) gave the title compound as a colourless foam (85 mg) $[\alpha]_D^{22}+188°$ (c 0.56, CHCl$_3$), $\lambda_{max}$(EtOH) 245.5 nm (ε, 29300) δ (CDCl$_3$) include 3.34 (S, 3H), 3.40 (m, 1H, M/Z=612 (M+).

The compound of Example 33 was prepared in a similar manner.

EXAMPLE 33

23-Ethoxy Factor B (147 mg) $[\alpha]_D^{21}+194°$ (c 0.72, CHCl$_3$), $\lambda_{max}$ (EtOH 245.5 nm (ε, 28500), δ(CDCl$_3$) include 3.26 (m, 1H), 3.47 (m, 1H), 3.65 (m, 1H), from Factor B (183 mg) and ethyl iodide (0.5 ml).

EXAMPLE 34

Factor A 23-Hemioxalate

Factor A (1 g, ca 70% purity) and calcium carbonate (1.5 g) were stirred together with dichloromethane (20 ml) at 21° and to the suspension was added in a single lot excess oxalyl chloride (1.0 ml). After 4–5 min. the mixture was treated with water (15 ml) and after a further 5 min with 2M HCl (10 ml) and ethyl acetate (70 ml). The organic phase was separated, washed with water and brine and then treated with decolourizing charcoal. After 5–10 min. the organic solution was filtered through phase-separating paper and the filtrate stripped of solvent. The residue in ether (50 ml) was clarified by filtration through "Hyflo" and removal of solvent gave a pale-yellow foam. Trituration of this material with diisopropyl ether (ca 7 ml) gave the title compound as a crystalline solid (750 mg) after washing the solid with diisopropyl ether and n pentane. The physical constants and spectral data are similar to those described for the product of Example 38.

EXAMPLE 35

Factor A

A solution of 23-hemioxalate Factor A (500 mg) in dichloromethane (30 ml) was vigorously stirred with aqueous sodium hydroxide (1.54 g in 30 ml H$_2$O) for 2 h at 21°. The organic phase was collected and the aqueous phase washed with a small volume of dichloromethane. The organic phases were combined, washed with 2M HCl, then dried (Na$_2$SO$_4$) and stripped of solvent to give the title compound (430 mg) as a foam. The compound was shown to be Factor A by comparison with an authentic sample of Factor A.

EXAMPLE 36

Factor A, 5-hemisuccinate

A solution of Factor A (306 mg) and succinic anhydride (60 mg) in dry pyridine (0.5 ml) was stirred at 22° for 24 h. The mixture was diluted with ether and the organic phase then washed with 2N. hydrochloric acid and brine. Evaporation of the dried ethereal layer gave a foam from which the title compound was isolated by reverse-phase preparative HPLC. The product in ether was precipitated as a white amorphous solid (86 mg) on addition of n-pentane $[\alpha]_D^{22}+125°$ (c 0.44, CHCl$_3$) $\lambda_{max}^{EtOH}$ 245 nm ($\epsilon_{max}$ 30,700), $\nu_{max}$ (CHBr$_3$) 3490 (OH) 3,300–2,200 (CO$_2$H), 1730 (acid carbonyl) and 1710 cm$^{-1}$ (ester); $\delta$ (CDCl$_3$) include 2.74 (s, 4H). m/z=712 (M+).

EXAMPLE 37

5-Acetoxy Factor A, 23-Hemioxalate

5-Acetoxy Factor A (600 mg), calcium carbonate (400 mg), and excess oxalyl chloride (0.8 ml) were stirred together in dry dichloromethane (20 ml) at 21° for 1¼ h. The mixture, diluted with ether, was poured into aqueous saturated sodium bicarbonate and was then stirred vigorously for 20 min before acidification to pH 2 with 2N hydrochloric acid. Evaporation of the dried (Na$_2$SO$_4$) organic phase gave a yellow gum which was dissolved in acetone and the solution then stirred with decolourizing charcoal. Following a conventional work up a colourless foam was obtained. This material was dissolved in ether (5 ml) and the solution diluted with n-pentane to precipitate the title compound as an amorphous white solid (403 mg), $[\alpha]_D^{23}+160°$ (c 0.40, CHCl$_3$), $\lambda_{max}^{EtOH}$ 245 nm ($\epsilon_{max}$30,800); $\nu_{max}$ (CHBr$_3$) 3530, 3445 (OH), 1802 (acid monomer), 1775 (acid dimer) and 1728 cm$^{-1}$ (esters); $\delta$ (CDCl$_3$) include ca 5.53 (obscured d., 1H), 5.12 (m, 1H), and 2.16 (s, 3H).

EXAMPLE 38

Factor A, 23-Hemioxalate

To a stirred and cooled (0°-5°) solution of 5-acetoxy Factor A, 23-nemioxalate (120 mg) in methanol (4 ml) was added dropwise a solution of sodium hydroxide (14 mg) in water (1 ml). After 1¾ h. the pale yellow solution was poured into ethyl acetate/2N-hydrochloric acid and the organic solution then collected, dried (Na$_2$SO$_4$) and stripped of solvent to provide an almost colourless foam. This material was dissolved in n-pentane containing a small volume of ether and the solution was then extracted with dilute aqueous potassium bicarbonate solution. The aqueous solution was acidified to pH 2 with 2N. hydrochloric acid and the precipitate then extracted into dichloromethane. Evaporation of the dried (Na$_2$SO$_4$) organic phase afforded a gum which was dissolved in a small volume of ether. Dilution of this solution with n-pentane gave the title compound (52 mg) as a while solid $[\alpha]_D^{23}+156°$ (c 0.69, CHCl$_3$); $\lambda_{max}^{EtOH}$ 244.5 nm ($\epsilon_{max}$, 28,200); $\nu_{max}$(CHBr$_3$) 3,360 to 3,600 (OH), 1805 (acid monomer) and 1720 cm$^{-1}$ (acid dimer and esters); $\delta$ (CDCl$_3$) include 4.30 (d, 5 Hz, 1H) and 5.14 (m, 1H).

EXAMPLE 39

Factor B, 23-hemioxalate

The title compound was prepared from Factor B in a manner similar to that described in Example 37. It was purified by reverse phase preparative HPLC and was obtained as an amorphous white powder (ether:n pentane) $[\alpha]_D^{23}+160°$ (c 0.20, CHCl$_3$); $\lambda_{max}$ 245.5 nm ($\epsilon_{max}$ 28,800); $\nu_{max}$(CHBr$_3$) 3460 (OH), 1800 (acid monomer), 1770 (acid dimer), 1724 and 1712 cm$^{-1}$ (esters); $\delta$ (CDCl$_3$) includes 5.15 (m, 1H) and 3.50 (s, 3H). m/z=670 (M+).

EXAMPLE 40

5-Acetoxy, 23-Ethyloxalyloxy Factor A

A solution of 5-acetoxy Factor A (320 mg) and excess ethyl oxalyl chloride (0.5 ml) in dry dichloromethane 16 ml) were stirred together in the presence of calcium carbonate 1300 mg) for 1 h. The mixture, diluted with ether, was poured into saturated sodium bicarbonate and was then stirred for 20 min before pouring into ethyl acetate. Evaporation of the dried (Na$_2$SO$_4$) organic phase provided a gum (325 mg) which in dichloromethane was introduced on to a column of Merck Kieselgel 60, 70–230 mesh silica (25 g) made up in the same solvent. Elution of the column with dichloromethane and then with dichloromethane:ether (95:5) afforded the title compound (265 mg) as a white foam $[\alpha]_D^{23}+157°$ (c 0.41, CHCl$_3$); $\lambda_{max}^{EtOH}$ 245 nm ($\epsilon_{max}$ 32,800); $\nu_{max}$ (CHBr$_3$) 3530, 3480 (OH), 1760 and 1735 cm$^{-1}$ (esters); $\delta$ (CDCl$_3$) includes 5.4 to 5.6 (m, 2H); 5.05 (m, 1H), 4.32 (q, 7 Hz, 2H), 2.13 (s, 3H) and 1.35 (t, 7 Hz, 3H).

EXAMPLE 41

23-Methyloxalyloxy Factor A

A solution of 5-acetoxy, 23-ethyloxalyloxy Factor A (50 mg) in methanol (1 ml) containing concentrated sulphuric acid (0.01 ml) was allowed to stand at 21° for 17 h. The mixture was then poured into ethyl acetate and the organic phase worked up for neutral material. The product was purified by chromatography over Merck Kieselgel 60, 70–230 mesh silica (15 g) using firstly dichloromethane and then dichloromethane:ether (9:1) as the eluting solvents. The title compound was obtained as a colourless gum (25 mg), $[\alpha]_D^{23}+147°$ (c 0.28, CHCl$_3$), $\lambda_{max}^{EtOH}$ 245 nm ($\epsilon_{max}$ 26,000); $\nu_{max}$ (CHBr$_3$) 3550, 3480 (OH), 1763, 1737 and 1710 cm$^{-1}$ (esters); $\delta$ (CDCl$_3$) include 4.29 (br.t., 7 Hz, 1H), 5.09 (m, 1H) and 3.88 (s, 3H).

EXAMPLE 42

Factor A, 5, 23-Bis hemioxalate

Factor A (200 mg) and excess oxalyl chloride (0.3 ml) were stirred together in dichloromethane (3 ml) in the presence of calcium carbonate (Calofort U, 300 mg) For 2 h. at 21°. The mixture was poured into ether/saturated aqueous sodium bicarbonate and was then stirred for a further 20 min. before acidification to pH 2 with dilute hydrochloric acid. Evaporation of the dried (Na$_2$SO$_4$) organic phase gave a gum from which the title compound was isolated by reverse-phase preparative HPLC and was obtained as an amorphous solid (ether:n-pentane) $[\alpha]_D^{22}+142°$ (c 0.41, CHCl$_3$); $\lambda_{max}^{EtOH}$ 245.5 nm ($\epsilon_{max}$ 29,200); $\nu_{max}$ (CHBr$_3$) 3550, 3440 (OH) 1800 and 1775 (acid monomer) and 1730 cm$^{-1}$ (esters); δ (CDCl$_3$) include 5.64 (m, 2H) and 5.13 (m, 1H).

EXAMPLE 43

Factor B, 23-chloroacetate

Factor B (600 mg) and excess chloroacetyl chloride (0.4 ml) were stirred together in dry dichloromethane (10 ml) in the presence of calcium carbonate (Calofort U, 380 mg) at 21° for 20 h. The mixture was then poured into ethyl acetate and the organic phase separated and washed with saturated aqueous sodium bicarbonate, 2N. hydrochloric acid and brine. Evaporation of the dried (Na$_2$SO$_4$) organic phase provided a yellow gum which on trituration with diisopropyl ether/petrol (40–60°) gave a crystalline solid. Recrystallization of this material from diisopropyl ether:petrol (40°–60°) afforded the title compound m.p. 224°–225°, $[α]_D^{23}$+77° (c 0.60, CHCl$_3$); $λ_{max}^{EtOH}$ 244.5 ($ε_{max}$30,250); $ν_{max}$ (CHBr$_3$) 3540, 3470 (OH), 1740 (chloroacetate) and 1710 cm$^{-1}$ (ester); δ (CDCl$_3$) includes 4.99 (m, 1H) and 3.49 (s, 3H). m/z=674, 676 (M+ $^{35}$Cl and $^{37}$Cl).

EXAMPLE 44

5-Acetoxy-23-cyclopropylcarbonyloxy factor A

A solution of 5-acetoxyfactor A (140 mg) in pyridine (1 ml) was treated with cyclopropanecarboxylic acid chloride (0.08 ml). After 3 hours the reaction mixture was partitioned between ethyl acetate and 2N hydrochloric acid. The organic phase was separated and was washed successively with 2N hydrochloric acid, and with saturated aqueous sodium bicarbonate solution. The organic solution was dried (Na$_2$SO$_4$) and the solvent was evaporated to leave an oil which was chromatographed over a column of silica (Merck Art 9385; 80 ml) made up in hexane (60°–80°)/ethyl acetate (3:1) and eluted with the same solvent. Appropriate fractions of the major component were combined and the solvent was evaporated to give the title compound as a foam (70 mg). $[α]_D^{22}$143° (c=0.54; CHCl$_3$); $λ_{max}^{CHCl_3}$ 250.2 (ε=20310); $ν_{max}$ (CHBr$_3$) 3550, 3470 (OH) and 1733, 1712 (ester); δ (CDCl$_3$) include 2.16 (s; 3H), 3.33 (m; 1H), 3.88 (d, J 10 Hz, 1H), 5.01 (m; 1H) and 5.5–5.6 (m; 2H).

The compounds of Examples 45–47 were prepared in a similar manner.

EXAMPLE 45

5-Acetoxy-23-cyclobutylcarbonyloxy Factor A

5-Acetoxy Factor A (0.5 g) and cyclobutanecarboxylic acid chloride (0.25 ml) gave the title compound as a foam (0.37 g). $[α]_D^{22}$+148° (c=0.635; CHCl$_3$); $λ_{max}^{CHCl_3}$ 250.2 (ε=17980); $ν_{max}$ (CHBr$_3$) 3540, 3460 (OH) and 1729, 1710 (ester); δ (CDCl$_3$) include 2.16 (s; 3H), 3.12 (quintet; J8 Hz; 1H), 3.32 (m; 1H), 3.91 (d; J 10 Hz; 1H), 4.9–5.1 (m; 2H), and 5.5–5.6 (m; 2H).

EXAMPLE 46

5-Acetoxy-23-cyclobutylcarbonyloxy Factor A

5-Acetoxy Factor A (0.28 g) and cyclopentylcarbonylchloride (0.2 ml) gave the title compound as a Foam (0.17 g). $[α]_D^{22}$+149° (c=0.475; CHCl$_3$); $λ_{max}^{CHCl_3}$250.2 nm (ε=19900); $ν_{max}$(CHBr$_3$) 3480 (OH), and 1730, 1710 (ester); δ (CDCl$_3$) include 2.16 (s; 3H), 2.74 (quintet, J 7 Hz, 1H), 3.32 (m; 1H), 3.90 (d, J 10 Hz, 1H), 4.94 (m; 1H) 5.5–5.6 (m; 2H).

EXAMPLE 47

5-Acetoxy-23-cyclohexylcarbonyloxy Factor A 5 5-Acetoxy Factor A (0.5 g) and cyclohexylcarbonyl chloride (0.25 ml) gave the title compound as a foam (0.51 g). $[α]_D^{20}$+143° (c=0.58; CHCl$_3$); $λ_{max}^{CHCl_3}$250.2(ε=21570); $ν_{max}$ (CHBr$_3$) 3540,3470 (OH), 1730, 1710 (ester); δ(CDCl$_3$) include 2.17 (s; 3H), 3.32 (m; 1H), 3.91 (d; J 10 Hz; 1H) 4.9–5.1 (m; 2H) 5.5–5.6 (m; 2H).

EXAMPLE 48

23-Cyclopropylcarbonyloxy Factor A

A stirred solution of 5-acetoxy-23-cyclopropylcarbonyloxy Factor A (230 mg) in methanol (15 ml) was cooled in an ice bath and was treated with 3% aqueous sodium hydroxide solution (0.5 ml). After 5 hours during which time the reaction was allowed to warm to room temperature, the solution was partitioned between ethyl acetate and 2N hydrochloric acid. The organic phase was separated, washed with 2N hydrochloric acid (×2), dried (Na$_2$SO$_4$) and the solvent was evaporated. The residue was chromatographed over a column of silica (Merck Art 9385; 150 ml) made up in hexane (60°–80°)/ethyl acetate and eluted with the same solvent. Appropriate Fractions of the major component were combined and the solvent was evaporated to leave the title ester as a foam (170 mg). $[α]_D^{22}$+146° (c=0.46; CHCl$_3$); $λ_{max}^{CHCl_3}$250.2 nm (ε=20090); $ν_{max}$ (CHBr$_3$) 3550, 3480 (OH) and 1709 (ester); δ(CHCl$_3$) include 3.26 (m; 1H), 3.88 (d, J 10 Hz, 1H), 4.29 (t, J 7 Hz, 1H) and 5.01 (m; 1H). The compounds of Examples 49–51 were prepared in a similar manner.

EXAMPLE 49

23-Cyclobutylcarbonyloxy Factor A

Deprotection of 5-acetoxy-23-cyclobutylcarbonyloxy Factor A (330 mg) gave the title ester as a foam (270 mg). $[α]_D^{20}$+149° (c=0.63; CHCl$_3$); $λ_{max}^{CHCl_3}$250.2 (ε=20430); $ν_{max}$ (CHBr$_3$) 3550, 3480 (OH), 1710 (ester) δ(CDCl$_3$) include 3.13 (quintet; J 8 Hz; 1H), 3.26 (m; 1H), 6 (m; 1H), 3.92 (d; J=10 Hz; 1H), 4.29 (t, J 7 Hz; 1H) 4.9–5.1 (m; 2H).

EXAMPLE 50

23-Cyclopentylcarbonyloxy Factor A

Deprotection of 5-acetoxy-23-cyclopentylcarbonyloxy Factor A (0.25 g) gave the title ester as a foam (0.215 g) $[α]_D^{20}$+141° (c=0.63; CHCl$_3$); $λ_{max}^{CHCl_3}$250.2 nm (ε=19990); $ν_{max}$ (CHBr$_3$) 3550, 3480 (OH), 1710 (ester); δ (CDCl$_3$) include 2.74 (quintet, J 7 Hz, 1H), 3.26 (m, 1H), 3.91 (d, J 10 Hz; 1H) 4.30 (t, J 7 Hz, 1H) 4.95 (m; 1H).

EXAMPLE 51

23-Cyclohexylcarbonyloxy Factor A

Deprotection of 5-acetoxy-23-cyclohexylcarbonyloxy Factor A (0.45 g) gave the title ester as a foam (0.42 g). $[α]_D^{20}$+132° (c=0.705; CHCl$_3$) $λ_{max}^{CHCl_3}$250.2(ε=18510); $ν_{max}$ (CHBr$_3$), 555, 3480 (OH), 1710 (ester); δ (CDCl$_3$) include 0.69 (d; J 7 Hz; 3H), 3.91 (d; J 10 Hz; 1H), 4.29 (t; J 7 Hz; 1H) 4.96 (m; 1H).

EXAMPLE 52

23-Cyclopropylcarbonyloxy-5-methoxycarbonyloxy Factor A

A solution of 23-cyclopropylcarbonyloxy Factor A (0.1 g) in dry dichloromethane (15 ml) was cooled in an ice bath and was treated with pyridine (0.2 ml), followed by a 1M solution of methylchloroformate in dichloromethane (0.3 ml). After 20 minutes the solution was diluted with dichloromethane and was washed with 2N hydrochloric acid, then dried over sodium sulphate and the solvent was evaporated. The residue was chromatographed over a column of silica (Merck, Art 9385; 100 ml) made up in hexane (60°–80°)/ethyl acetate (13:1) and eluted with the same solvent. Appropriate Fractions of the major component were combined and the solvent was evaporated to leave the title compound as a foam (0.106 g). $[\alpha]_D^{20} + 149°$ (c=0.63; CHCl$_3$); $\lambda_{max}^{CHCl_3}$ 250.2 ($\epsilon_{max}$ (CHBr$_3$) 3470 (OH), 1745 (carbonate), 1710 (ester), 998 (C-O); $\delta$ (CDCl$_3$) include 5.56 (s; 1H), 5.01 (ml 1H), 3.88 (d; J 10 Hz; 1H), 3.83 (s; 3H), 0.67 (d; J 7 Hz; 3H).

The compounds of Examples 53-55 were prepared in a similar manner:

EXAMPLE 53

23-Cyclobutylcarbonyloxy-5-methoxycarbonyloxy Factor A (0.13 g)

$[c]_D^{20} + 149°$ (c=0.515;CHCl$_3$);$\lambda_{max}^{CHCl_3}$ 250.6 ($\epsilon$=20100); $\epsilon_{max}$ (CHBr$_3$) 3480 (OH), 1744 (carbonate), 1710 (ester), 996 (C-O); $\delta$ (CDCl$_3$) include 5.56 (s; 1H), 4.96 (m; 1H), 3.92 (d; J 10 Hz; 1H), 3.83 (s; 3H), 3.13 (quintet; J 8 Hz; 1H), 0.70 (d; ]7 Hz; 3H), From 23-cyclobutylcarbonyloxy Factor A (0.12 g).

EXAMPLE 54

23-Cyclopentylcarbonyloxy-5-methoxycarbonyloxyfactor A (0.115 g)

$[\alpha]_D^{20} + 141°$ (c=0.505; CHCl$_3$); $\lambda_{max}^{CHCl_3}$ 250.2 ($\epsilon_{max}$ (CHBr$_3$) include 5.56 (s; 1H), 4.95 (m; 1H), 3.91 (d; J 10 Hz; 1H), 3.83 (s; 3H), 2.74 (quintet; ]8 Hz; 1H), 0.69 (d; J 7 Hz; 3H), From 23-cyclopentylcarbonyloxy Factor A (0.106 g).

EXAMPLE 55

23≃Cyclohexylcarbonyloxy-5-methoxycarbonyloxy Factor A (0.1 g)

$[\alpha]_D^{20} + 136°$ (c=0.47; CHCl$_3$); $\lambda_{max}^{CHCl_3}$ 250.2 ($\epsilon_{max}$ CHBr$_3$) 3470 (OH), 1744 (carbonate), 1710 (ester), 996 (C-O); $\delta$ (CDCl$_3$) include 5.57 (s; 1H) 4.97 (m; 2H), 3.92 (d; J 10 Hz; 1H), 3.84 (s; 3H), 0.69 (d; J 7 Hz; 3H), from 23-cyclohexylcarbonyloxy factor A 0.108 g).

EXAMPLE 56

Factor A, 5,23-di-n-butyrate

A solution of Factor A (306 mg), n-butyric anhydride (0.33 ml) and 4-dimethylaminopyridine (244 mg) in pyridine (5 ml) was stirred at 20° for 18 hours, and then poured into a mixture of ethyl acetate and 2N-hydrochloric acid (50 ml of each). The organic phase was washed with 2N-hydrochloric acid, saturated sodium bicarbonate (25 ml), and brine (25 ml), and dried (magnesium sulphate), and evaporated to dryness. The residue was purified by chromatography over Kieselgel 60 (40 g). Elution of the column with light petroleum:ethyl acetate (5:1) gave the title compound (200 mg) as a colourless foam, $[\alpha]_D^{20} + 144°$ (c 1.13, CHCl$_3$), $\lambda_{max}$ (EtOH) 245 nm ($\nu$31,800), $\nu_{max}$ (CHBr$_3$) 1720 cm$^{-1}$ (esters) $\delta$ (CDCl$_3$) include 5.5 to 5.6 (m, 2H), 4.94 (m, 1H), 3.92 (d, J 10 Hz, 1H), 2.39 (t, J 7 Hz, 2H), 2.28 (t, J 7 Hz, 2H) and 0.70 (d, J 7 Hz, 3H), m/z=752 (M+).

The compounds of Examples 58,59,62,64,66,67 and 96 were prepared in a similar manner.

EXAMPLE 57

Factor A, 23-n-butyrate

A solution of Factor A 5,23-n-butyrate (160 mg) In methanol (10 ml) was stirred at OD and 1M-sodium hydroxide (0.25 ml) was added. The resulting solution was stirred for 90 minutes at 0° to 5°, then more 1M sodium hydroxide 0.25 ml) was added, and stirring was continued for a further 4 hours. The solution was poured into a mixture of ethyl acetate (150 ml) and 2N-hydrochloric acid (25 ml), and the organic phase was washed with water, and brine, and dried (magnesium sulphate), and evaporated to dryness. The residue was purified by chromatography over Kieselgel 60 (20 g). Elution of the column with light petroleum:ethyl acetate (2:1) gave the title compound (68 mg) as a colourless foam, $[\alpha]_D^{20} + 164°$ co 1.03, CHCl$_3$), $\lambda_{max}$ (EtOH) 244.5 nm ($\epsilon$ 29,600), $\nu_{max}$ (CHBr$_3$) 3550 and 3470 (OH), and 1710 cm$^{-1}$ (esters), $\delta$ (CDCl$_3$) Include 4.93 (m, 1H), 4.28 (t, J 7 Hz, 1H), 3.91 (d, J 10 Hz, 1H), 2.28 (t, J 7 Hz, 2H), 1.65 (m, 2H), 0.94 (t, J 7 Hz, 3H) and 0.69 (d, J 7 Hz, 3H), m/z=682 (M+).

The compounds of Examples 61,63,65,68,90 and 97 were prepared in a similar manner.

EXAMPLE 58

Factor A, 5-acetate, 23-n-butyrate (143 mg)

$[\alpha]_D^{20} + 152°$ (c 0.7, CHCl$_3$), $\lambda_{max}$(EtOH) 244 nm ($\epsilon$ 27,300), $\nu_{max}$ (CHBr$_3$) 3490 (OH) and 1720 cm$^{-1}$ (esters), $\delta$ (CDCl$_3$) include 5.5 to 5.6 (m, 2H), 4.95 (m, 1H), 3.92 (d, J 10 Hz, 1H), 2.29 (m, 2H), 2.16 (s, 3H), 0.96 (t, J 7 Hz, 3H) and 0.70 (d, J 7 Hz, 3H), From Factor A, 5-acetate (218 mg) and n-butyric anhydride (0.16 ml).

EXAMPLE 59

Factor A, 5-acetate, , 23-diisobutyrate 1300 mg)

$[\alpha]_D^{20} + 157°$ (c 0.61, CHCl$_3$), $\lambda_{max}$ (EtOH) 244 nm ($\epsilon$29,200), $\nu_{max}$ (CHBr$_3$) 3470 (OH) and 1720 cm$^{-1}$ (esters), $\delta$ (CDCl$_3$) include 5.53 (m, 2H), 4.95 (m, 1H), 3.93 (d, J 10 Hz, 1H), 2.8 to 2.4 (m, 2H), 1.23 (d, 7 Hz, 6H), 1.20 (d, J 7 Hz, 6H) and 0.70 (d, J 7 Hz, 3H), From Factor A (306 mg) and isobutyryl chloride (0.2 ml).

EXAMPLE 60

Factor A, 5-acetate, 23-isobutyrate.

A solution of Factor A, 5-acetate (131 mg), isobutyryl chloride (0.05 ml), pyridine (0.1 ml) and 4-dimethylaminopyridine 125 mg) in dry dichloromethane (10 ml) was stirred al 20° for 16 hours. The solution was diluted with dichloromethane (30 ml), washed with 2N-hydrochloric acid, and dried (magnesium sulphate), and evaporated to dryness. The residue was purified by chromatography over Kieselgel 60 (15 g). Elution of the column with liquid petroleum:ethyl acetate (4:1) gave the title compound (57 mg) as a colourless Foam, $[\alpha]_D^{20} + 159°$ (c 0.61, CHCl$_3$), $\lambda_{max}$ (EtOH) 244 nm ($\epsilon$ 30,400), $\nu_{max}$(CHBr$_3$) 3480 (OH), and 1713 cm$^{-1}$ (esters), $\delta$ (CDCl$_3$) include 5.5 to 5.6 (m, 2H), 4.95 (m, 1H), 3.93 (d, J 10 Hz, 1H), 2.55 (septet, J 7 Hz, 1H), 2.17 (s, 3H), 1.20 (d, J 7 Hz, 6H) and 0.70 (d, J 7 Hz, 3H).

EXAMPLE 61

Factor A, 23-isobutyrate (280 mg)

$[\alpha]_D^{20} +162°$ (c 0.65, CHCl$_3$), $\lambda_{max}$ (EtOH) 244 nm ($\epsilon$ 31,000), $\nu_{max}$ (CHBr$_3$) 3560 and 3480 (OH), and 1712 cm$^{-1}$ (esters), $\delta$ (CDCl$_3$) include 4.95 (m, 1H), 4.29 (t, J 7 Hz, 1H), 3.92 (d, J 10 Hz, 1H), 2.54 (septet, J 7 Hz, 1H), 1.19 (d, J 7 Hz, 6H) and 0.69 (d, J 7 Hz, 3H), from Factor A, 5-acetate, 23-isobutyrate (420 mg).

EXAMPLE 62

Factor A, 5-acetate, 23-heptanoate (437 mg)

$[\alpha]_D^{20} +153°$ (o 0.6, CHCl$_3$), $\lambda_{max}$ (EtOH) 244 nm ($\epsilon$ 29,700), $\nu_{max}$ (CHBr$_3$) 3490 (OH), and 1730 and 1712 cm$^{-1}$ (esters), $\delta$ (CDCl$_3$) include 5.5 to 5.6 (m, 2H), 4.93 (m, 1H), 3.91 (d, J 10 Hz, 1H), 2.28 (t, J 8 Hz, 2H), 2.13 (s, 3H), 0.86 (t, J 7 Hz, 3H) and 0.68 (d, J 7 Hz, 3H), from Factor A, 5-acetate (491 mg) and heptanoyl chloride (0.31 ml).

EXAMPLE 63

Factor A, 23-heptanoate (230 mg)

$[\alpha]_D^{20} +149°$ (c 0.7, CHCl$_3$), $\lambda_{max}$ (EtOH) 244 nm ($\epsilon$ 30,400), $\nu_{max}$ (CHBr$_3$) 3550 and 3480 (OH), and 1712 cm$^{-1}$ (esters), $\delta$ (CDCl$_3$) include 4.94 (m, 1H), 4.29 (t, J 7 Hz, 1H), 3.92 (d, ]10 Hz, 1H), Z.}0 (t, ]8 Hz, 2H), 0.88 (t, ]7 Hz, 3H) and 0.69 (d, (d, J 10 Hz, 1H), 2.30 (t, J 8 Hz, 2H), 0.88 (t, J 7 Hz, 3H) and 0.69 (d, J 7 Hz, 3H), from Factor A, 5-acetate, 23-heptanoate (387 mg)

EXAMPLE 64

Factor A, 5-acetate, 23-pivaloate (70 mg)

$[\alpha]_D^{20} +159°$ (c 0.69, CHCl$_3$) $\lambda_{max}$ (EtOH) 244 nm ($\epsilon$ 29,900), $\nu_{max}$ (CHBr$_3$) 3470 (OH) and 1730 and 1710 cm$^{-1}$ (esters), $\delta$(CDCl$_3$) include 5.5 to 5.6 (m, 2H), 4.95 (m, 1H), 3.91 (d, J 10 Hz, 1H), 2.16 (s, 3H), 1.22 (s, 9H), and 0.68 (d, J 7 Hz, 3H), from Factor A, 5-acetate (131 mg) and pivaloyl chloride (0.06 ml).

EXAMPLE 65

Factor A, 23-pivaloate (214 mg)

$[\alpha]_D^{20} +152°$ (c 0.74, CHCl$_3$), $\lambda_{max}$ (EtOH) 244 nm ($\epsilon$27,500), $\nu_{max}$ (CHBr$_3$) 3550 and 3500 (OH), and 1710 cm$^{-1}$ (esters), $\delta$(CDCl$_3$) include 4.95 (m, 1H), 4.29 (broad s, 1H), 3.91 (d, J 10 Hz, 1H), 1.23 (s, 9H) and 0.69 (d, J 7 Hz, 3H), from Factor A, 5-acetate, 23-pivaloate (315 mg).

EXAMPLE 66

Factor A, 5-acetate, 23-benzoate (180 mg)

$[\alpha]_D^{20} +153°$ (c 0.59, CHCl$_3$), $\lambda_{max}$ (EtOH) 236 nm ($\epsilon$ 36,200), $\nu_{max}$ (CHBr$_3$) 3460 (OH) and 1730 and 1707 cm$^{-1}$ (esters), $\delta$ (CDCl$_3$) include 8.21(d,J7 Hz,2H), 7.56 (t,J7 Hz,1H), 7.44 (t, J 7 Hz, 2H), 5.5 to 5.6 (m, 2H), 4.07 (d, J 10 Hz, 1H), 2.17 (s, 3H) and 0.75 (d, J 7 Hz, 3H), from Factor A, 5-acetate (327 mg) and benzoic anhydride (339 mg).

EXAMPLE 67

Factor A, 5,23-dibenzoate (370 mg) and 5-benzoate (200 mg)

From Factor A (613 mg) and benzoyl chloride (0.35 ml); initial fractions gave the title dibenzoate, $[\alpha]_D^{20} +86°$ (c 0.65, CHCl$_3$), $\lambda_{max}$(EtOH) 236 nm ($\epsilon$ 46,200), $\nu_{max}$ (CHBr$_3$) 3480 (OH), 1710 (esters), and 1602 and 1585 cm$^{-1}$ (phenyl), $\delta$ (CDCl$_3$) include 8.2 to 8.0 (m, 4H), 7.7 to 7.5 (m, 2H), 7.46 (t, J 7 Hz, 4H), 5.61 (s, 1H), 4.07 (d, J 10 Hz, 1H) and 0.76 (d, J 7 Hz, 3H).

Further fractions gave the title benzoate, $[\alpha]_D^{20} +80°$ (c 0.61, CHCl$_3$), $\lambda_{max}$ (EtOH) 237 nm ($\epsilon$ 39,200), $\nu_{max}$ (CHBr$_3$) 3500 (OH), 1712 (esters), and 1601 and 1585 cm$^{-1}$ (phenyl), $\delta$ (CDCl$_3$) include 8.09 (d, J 7 Hz, 2H), 7.58 (t, J 7 Hz, 1H), 7.45 (t, J 7 Hz, 2H), 5.60 (s, 1H), 3.83 (m, 1H), 3.76 (d, J 10 Hz, 1H) and 0.81 (d, J 7 Hz, 3H).

EXAMPLE 68

Factor A, 23-benzoate (90 mg)

$[\alpha]_D^{20} +146°$ (c 0.63, CHCl$_3$), $\lambda_{max}$ (EtOH) 236 nm ($\epsilon$ 33,800), $\nu_{max}$ (CHBr$_3$) 3560 and 3480 (OH), and 1709 cm$^{-1}$ (esters), $\delta$ (CDCl$_3$) include 8.10 (d, J 7 Hz, 2H), 7.55 (t, J 7 Hz, 1H), 7.44 (t, J 7 Hz, 2H) 4.29 (t, J 7 Hz, 1H), 4.07 (d, J 10 Hz, 1H) and 0.75 (d, J 7 Hz, 3H), from Factor A 5,23-dibenzoate (315 mg).

EXAMPLE 69

Factor A, 5-chloroacetate

A solution of Factor A (123 mg) and pyridine (0.1 ml) in dry dichloromethane (5 ml) was stirred at 0° and chloroacetyl chloride (0.3 ml of 1M-solution in dichloromethane) was added. The resulting solution was stirred at 0° for 15 minutes, then more chloroacetyl chloride (0.1 ml of 1M-solution) was added, and stirring was continued for a further 15 minutes. The solution was diluted with dichloromethane (50 ml), then washed with 2N-hydrochloric acid 12×20 ml), and saturated sodium bicarbonate (20 ml), and dried (magnesium sulphate), and evaporated to dryness. The residue (140 mg) was purified by chromatography over Kieselgel 60 (15 g). Elution of the column with light petroleum:ethyl acetate (4:1) gave the title compound (90mg) as a colourless foam, $[\alpha]_D^{20} +143°$ (c 1.11, CHCl$_3$), $\lambda_{max}$ (EtOH) 245.5 nm ($\epsilon$ 30,400), $\nu_{max}$ (CHBr$_3$) 3500 (OH), 1760 (chloroacetate) and 1710 cm$^{-1}$ (ester), $\delta$ (CDCl$_3$) include 5.5 to 5.6 (m, 2H) 4.18 (s, 2H), ca. 3.81 (m, 1H), 3.74 (d, J 10 Hz, 1H) and 0.80 (d, J 7 Hz, 3H), m/z=688 (M+, $^{35}$Cl).

The compounds of Examples 71–75, 82,83,85,87,89,91,93,95 and 98–102 were prepared in a similar manner.

EXAMPLE 70

Factor A, 5-chloroacetate, 23-ketone

A solution of Factor A, 5-chloroacetate (276 mg) and pyridinium dichromate (602 mg) In dry N,N-dimethylformamide (10 ml) was stirred at 20° For 48 hours, and then poured into a mixture of ethyl acetate (50 ml) and 2N-hydrochloric acid(25 ml). The organic phase was washed with 2N-hydrochloric acid, and saturated sodium bicarbonate, and dried (magnesium sulphate), and evaporated to dryness. The residue was purified by chromatography over Kieselgel 60 (25 g). Elution of the column with light petroleum:ethyl acetate (4:1) gave the title compound (85 mg) as a colourless foam, $[\alpha]_D^{20} +120°$ (c 1.05, CHCl$_3$), $\lambda_{max}$ (EtOH) 245 nm ($\epsilon$ 26,500), $\nu_{max}$ $_{(CHBr3)}$ 3480 (OH), 1760 (chloroacetate) and 1715 cm$^{-1}$ (ester and ketone), J (CDCl$_3$) include 5.5 to 5.7 (m, 2H), 4.17 (s, 2H), 3.72 (d, $\delta$10 Hz, 1H), 2.50 (s 2H) and 0.85 (d, J 7 Hz, 3H), m/z=686 (M+, $^{35}$Cl).

The compounds of Examples 84, 86 and 104 were prepared in a similar manner.

EXAMPLE 71

Factor A, 5-bromoacetate (447mg)

$[\alpha]_D^{20}$ +132° (c 0.77, CHCl$_3$), $\lambda_{max}$ (EtOH) 245.5 nm ($\epsilon$31,500), $\nu_{max}$ (CHBr$_3$) 3495 (OH), 1730 (bromoacetate) and 1712 cm$^{-1}$ (ester), δ (CDCl$_3$) include 5.5 to 5.6 (m, 2H), 3.97 (d, J 12 Hz, 1H), 3.90 (d, J 12 Hz,1 H), 3.81 (m, 1H), 3.75 (d, J 10 Hz, 1H) and 0.81 (d, J 7 Hz, (3H), from Factor A (613 g) and bromoacetyl bromide (0.13 ml).

EXAMPLE 72

Factor A, 5-n-butyl carbonate, 23-ketone (75mg)

$[\alpha]_D^{20}$+103° (c 0.7, CHCl$_3$), $\lambda_{nax}$(EtOH) 245 nm ($\epsilon$ 26,200), $\nu_{max}$ (CHBr$_3$) 3480 (OH), 1738 (carbonate), and 1720 cm$^{-1}$ (ester and ketone), δ (CDCl$_3$) include 5.56 (s, 1H), 4.3 to 4.0 (m, 3H), 3.71 (d, J 10 Hz, 1H), 0.93 (t, J 7 Hz, 3H) and 0.86 (d, J 7 Hz, 3H).

From Factor A, 23-ketone (92 mg) and n-butyl chloroformate (0.04 ml).

EXAMPLE 73

Factor A, 5-methyl carbonate, 23-isobutyrate (78 mg)

$[\alpha]_D°$+166° (c 0.7, CHCl$_3$), $\lambda_{max}$ (EtOH) 244 nm ($\epsilon$ 29,400), $\nu_{max}$ (CHBr$_3$) 3480 (OH), 1743 (carbonate) and 1712 cm$^{-1}$ (esters), δ (CDCl$_3$) include 5.55 (s, 1H), 4.94 (m, 1H), 3.92 (d, J 10Hz, 1H), 3.83 (s, 3H), 2.54 (sepet, J 7 Hz, 1H), 1.20 (d, J 7 Hz, 6H) and 0.69 (d, J 7 Hz, 3H), from Factor A, 23-isobutyrate (103 mg) and ethyl chloroformate (0.3 ml of a 1M-solution in dichloromethane).

EXAMPLE 74

Factor A, 5-benzyl carbonate, 23-propionate (66 mg)

$[\alpha]_D°$+123° (c 0.6, CHCl$_3$), $\lambda_{max}$ (EtOH) 244 nm ($\epsilon$ 30,000), $\nu_{max}$ (CHBr$_3$) 3540 and 3470 (OH), 1720 cm$^{-1}$ (esters and carbonate) δ (CDCl$_3$) include 7.5 to 7.3 (m, 5H), 5.56 (s, 1H), 4.95 (m, 1H), 3.92 (d, J 10 Hz, 1H), 2.33 (q, J 7 Hz, 3H) and 0.70 (d, J 7 Hz, 3H), from Factor A, 23-propionate (100 mg) and benzyl chloroformate (0.05 ml). chloroformate (0.05 ml).

EXAMPLE 75

Factor A, 5-methyl carbonate, 23-heptanoate (120 mg)

$[\alpha]_D°$+157° (c 0.69, CHCl$_3$), $\lambda_{max}$ (EtOH) 244 nm ($\epsilon$ 31,600), $\nu_{max}$ (CHBr$_3$) 3480 (OH), 1743 (carbonate) and 1712 cm$^{-1}$ (esters), δ (CDCl$_3$) include 5.56 (s, 1H), 4.95 (m, 1H), 3.92 (d, J 10 Hz, 1H), 3.83 (s, 3H), 2.30 (t, J 7 Hz, 2H), 0.88 (t, J 7 Hz, 3H) and 0.69 (d, J 7 Hz, 3H), from Factor A, 23-heptanoate (145 mg) and methyl chloroformate (0.4 ml of a 1M-solution in dichloromethane).

EXAMPLE 76

Factor A, 5,23-di-chloroacetate.

A mixture of Factor A, 5-chloroacetate (365 mg), chloroacetyl chloride (0.21 ml) and calcium carbonate (265 mg) in dry dichloromethane (15 ml) was stirred at 20° for 48 hours. The resulting suspension was diluted with dichloromethane (50 ml), then washed with 2N-hydrochloric acid and saturated sodium bicarbonate, and dried (magnesium sulphate), and evaporated to dryness. The residue was purified by chromatography over Kieselgel 60 (30 g). Elution of the column with light petroleum:ethyl acetate 4:1 gave the title compound (167 mg) as a colourless foam, $[\alpha_D^{20}]$+151° (c 1.17, CHCl$_3$), $\lambda_{max}$ (EtOH) 245.5 nm ($\epsilon$ 29,400 ), $\nu_{max}$ (CHBr$_3$) 3470 (OH) and 1725 cm$^{-1}$ (esters), δ(CDCl$_3$) include 5.5 1to 5.6 (m, 2H), 5.00 (m, 1H), 4.17 (s, 2H), 4.10 (d, J 15 Hz, 1H), 4.02 (d, J 15 Hz, 1H), 3.92 (d, J 10 Hz, 1H) and 0.73 (d J 7 Hz, 3H), m/z=764(M+, $^{35}$Cl).

The compounds of Examples 77–8192 and 94 were prepared in a similar manner.

EXAMPLE 77

Factor A, 5-acetate 23-chloroacetate (447 mg)

$[\alpha]_D°$+161° (c 0.94, CHCl$_3$), $\lambda_{max}$ (EtOH) 245 nm ($\epsilon$ 29,900), $\nu_{max}$ (CHBr$_3$) 3470 (OH) and 1730 cm$^{-1}$ (esters), δ (CDCl$_3$) include 5.5 to 5.6 (m, 2H), 4.99 (m, 1H), 4.10 (d, J 15 Hz, 1H), 4.02 (d, J 15 Hz, 1H), 3.92 (d J 10 Hz, 1H), 2.17 (s, 3H), and 0.73 (d, J 7 Hz, 3H), m/z=730 (M+, $^{35}$CL), from Factor A, 5-acetate (655 mg) and chloracetyl chloride (0.4 ml).

EXAMPLE 78

Factor A, 5-acetate 23-bromoacetate (210 mg)

$[\alpha]_D^{20}$+151° (c 0.91, CHCl$_3$), $\lambda_{max}$ (EtOH) 245 nm ($\epsilon$ 28,900), $\nu_{max}$ (CHBr$_3$) 3470 (OH) and 1728 cm$^{-1}$ (esters), δ (CDCl$_3$) include 5.5 to 5.6 (m, 2H), 4.94 (m, 2H), 3.93 (d, J 10 Hz, 1H), 3.89 (d, J 13 Hz, 1H), 3.80 (d J 13 Hz, 1H), 2.16 (s, 3H), and 0.75 (d, J 7 Hz, 3H), from Factor A, 5-acetate (655 mg) and bromoacetyl bromide 0.44 ml.

EXAMPLE 79

Factor A, 5,23-di-bromoacetate (430 mg)

$[\alpha]_{Dhu}°$+132° (c 1.04, CHCl$_3$), $\lambda_{max}$ (EtOH) 245,5 nm ($\epsilon$ 30,600 ), $\nu_{max}$ (CHBr$_3$) 3460 (OH) and 1726 cm$^{-1}$ (esters), include 5.5 to 5.6 (m, 2H), 4.98 (m, 2H), 4.0 to 3.7 (m, 6H) and 0.74 (d, J 7 Hz, 3H), from Factor A (613 mg) and bromoacetyl bromide (0.44 ml).

EXAMPLE 80

Factor A, 23-methoxyacetate (92 mg)

$[\alpha]_{Dhu}°$+157° (c 0.75, CHCl$_3$), $\lambda_{max}$ (EtOH) 244 nm ($\epsilon$ 32,300), $\nu_{max}$ (CHBr$_3$) 3560 and 3480 (OH), 1740 (methoxyacetate) and 1712 cm$^{-1}$ (ester), δ (CDCl$_3$) include 5.01 (m, 1H), 4.28 (t, J 7 Hz, 1H), 4.01 (s, 2H), 3.89 (d, J 10 Hz, 1H), 3.46 (s, 3H) and 0.71 (d, J 7 Hz, 3H), from Factor A (184 mg) and methoxyacetyl chloride (0.3 ml).

EXAMPLE 81

Factor A, 23-phenoxyacetate (112 mg)

$[\alpha]_D°$+129° (C 0.75, CHCl$_3$), $\lambda_{max}$(EtOH) 244 nm ($\epsilon$ 25,900), $\nu_{max}$ (CHBr$_3$) 3550 and 3470 (OH), and 1745 and 1708 cm$^{-1}$ (esters), δ (CDCl$_3$) include 7.30 (t, 3 8 Hz, 2H) 7.00 (t, J 8 Hz, 1H), 6.94 (d, J Hz, 2H), , 5.02 (m, 1H), 4.68 (d, J 16 Hz, 1H), 4.58 (d, J 16 Hz, 1H), 4.30 (d, J 7 Hz, 1H), 3.92 (d, J 10 Hz, 1H) and 0.67 (d, J 7 Hz, 3H, from Factor A (184 mg) and phenoxyacetyl chloride (0.38 ml).

EXAMPLE 82

Factor A, 5-acetate 23-propionate (60 mg)

$[\alpha]_D° +173°$ (c 0.85, CHCl$_3$), $\lambda_{max}$ (EtOH) 245 nm ($\epsilon$ 28,100), $\nu_{max}$ (CHBr$_3$) 3460 (OH) and 1725 cm$^{-1}$ (esters), $\delta$(CDCl$_3$) include 5.5 to 5.6 (m, 2H), 4.94 (m, 1H), 3.91 (d, J 10 Hz, 1H), 2.31 (d, J 7 Hz, 2H), 2.16 (s, 3H), 1.15 (t, J 7 Hz, 3H) and 0.69 (d, J 7 Hz, 3H), from Factor A, 23-propionate (100 mg) and acetyl chloride (0.5 ml of 1M-solution in dichloromethane).

EXAMPLE 83

Factor A, 5-methyl carbonate (475 mg)

$[\alpha]_D° +146°$ (c, 1.05, CHCl$_3$), $\lambda_{max}$ (EtOH) 244 nm ($\epsilon$29,400), $\nu_{max}$ (CHBr$_3$) 3500 (OH), 1742 (carbonate), and 1710 cm$^{-1}$ (ester), $\delta$(CDCl$_3$) include 5.56 (s, 1H), 3.82 (s, 3H), 3.76 (d, J10 Hz, 1H) and 0.81 (d, J7 Hz, 3H), m/z=670 (M+), from Factor A (613 mg) and methyl chloroformate (0.2 ml).

EXAMPLE 84

Factor A, 5-methyl carbonate, 23-ketone (110 mg)

$[\alpha]_D^{20}$ 129° (c, 0.84, CHCl$_3$), $\lambda_{max}$ (EtOH) 245.5 nm ($\epsilon$ 28,900), $\nu_{max}$ (CHBr$_3$) 3320 to 3600 (OH), 1745 (carbonate) and 1715 cm$^{-1}$ (ester and ketone) $\delta$ (CDCl$_3$) include 5.56 (s, 1H), 3.83 (s, 3H), 3.70 (d, J 10 Hz, 1H), 2.50 (s, 2H), and 0.86 (d, J 7 Hz, 3H), m/z=668 (M+), from Factor A, 5-methyl carbonate (282 mg).

EXAMPLE 85

Factor A, 5-(2,2,2-trichloroethyl)carbonate (238 g).

$[\alpha]_D° +119°$ (c, 0.93, CHCl$_3$), $\lambda_{max}$ (EtOH) 245 nm ($\epsilon$30,700), $\nu_{max}$ (CHBr$_3$) 3500 (OH), 1755 (carbonate), and 1710 cm$^{-1}$ (ester), $\delta$)CDCl$_3$) include 5.60 (s, 1H), 4.90 and 4.75 (ABq, J12 Hz). 2H), 2H), 3.81 (m, 1H), 3.75 (d, J10 Hz, 1H), and 0.80 (d, J 7 Hz, 3H), m/z=786 (M+, $^{35}$Cl), from Factor A (306 mg) and 2,2,2-trichloroethyl chloroformate (0.9 ml of a 1M-solution in dichloromethane).

EXAMPLE 86

Factor A, 5-(2,2,2-trichloroethyl)carbonate, 23-ketone (65 mg)

$[\alpha]_D° +\nu°$ (c, 1.07 CHCl$_3$), $\lambda_{max}$ (EtOH) 245.5 nm, ($\epsilon$28,300), $\nu_{max}$ (CHBr$_3$) 3300 to 3600 (OH), 1755 (carbonate), and 1710 cm$^{-1}$ (ester and ketone), $\delta$(CDCl$_3$) include 5.61 (s, 1H), 4.90 and 4.75 (ABq, J12 Hz, 2H), 3.72 (d, J10 Hz, 1H), 2.51 (s, 2H) and 0.87 (d, J7 Hz, 3H), m/z=784 (M+$^\pm$Cl), from Factor A, 5-(2,2,2-trichloroethyl) carbonate (186 mg).

EXAMPLE 87

Factor A, 5,23 -di-(2,2,2-trichloroethyl)carbonate (362 mg)

$[\alpha]_D^{22}+110°$ 0.94, CHCl$_3$), $\lambda_{max}$ (EtOH) 244 nm ($\epsilon$28,000), $\nu_{max}$ (CHBr$_3$) 3550 and 3460 (OH), 1750 (carbonate), and 1710 cm$^{-1}$ (ester), $\delta$(CDCl$_3$) include 5.60 (s, 1H), 4.89 and 4.75 (ABq, J12 Hz, 2 H), 4.85 5 (m, 1H), 4.81 and 4.71 (ABq, J14 Hz, 2H), and 0.79 (d. J7 Hz, 1H), from Factor A 1306 mg) and 2,2,2-trichloroethyl chloroformate (0.14 ml).

EXAMPLE 88

Factor A, 23-(2,2,2-trichloroethyl)carbonate

A solution of Factor A, 5,23-di-(2,2,2-trichloroethyl)-carbonate (200 mg) in dioxan (10 ml) was stirred at ca. 20°, and 1M-sodium hydroxide 0.5 ml) was added. The resulting solution was stirred for 30 minutes, then more 1M-sodium hydroxide (1 ml) was added, and stirring was continued or a further 1 hour. The solution was diluted with ethyl acetate (50 ml), washed with 2N-hydrochloric acid, and dried (magnesium sulphate), and evaporated to dryness. The residue was purified by chromatography over Kieselgel 60 (15 g). Elution of the column with light petroleum:ethylacetate (2:1) gave the title compound (80 mg), as a colourless foam, $[\alpha]_D°+142°$ (c, 0.92 , CHCl$_3$) $\lambda_{max}$ EtOH) 245 nm ($\epsilon$29,200), $\nu_{max}$(CHBr$_3$) 3560 and 3500 (OH), 1745 (carbonate), and 1710 cm$^{-1}$ (ester), $\delta$(CDCl$_3$) include 5.40 (s, 1H), 4.80 and 4.70 (ABq, J 14 Hz, 2H), 4.28 (m, 1H) and 0.79 (d, J7 Hz, 3H).

EXAMPLE 89

Factor A, 5-acetate,23-(2,2,2-trichloroethyl)carbonate (385 mg)

$[\alpha]_D^{20}+140°$ (c, 107, CHCl$_3$), $\lambda_{max}$ (EtOH) 245.5 nm, ($\epsilon$ 29,200), $\nu_{max}$ (CHBr$_3$) 3300 to 3620 (OH), 1738 (carbonate), and 1720 cm$^{-1}$ (ester), $\delta$ (CHCl$_3$) include 5.53 (s, 1H), 4.81 and 4.70 (Abq, J14 Hz, 2 H), 4.84 (m, 1H), 3.98 (d, J 10 Hz, 1H), 2.16 (s, 3H) and 0.79 (d, J 7 Hz, 3H), from Factor A, 5-acetate (393 mg) and 2,2,2-trichloroethyl chloroformate (2 ml of 1M-solution in dichloromethane).

EXAMPLE 90

Factor A, 23-methyl carbonate (155 mg)

$[\alpha]_{Dhu}° +169°$ (c, 0.81, CHCl$_3$), $\lambda_{max}$ (EtOH) 245 nm ($\epsilon$ 26,600), $\nu_{max}$ (CHBr$_3$) 3500 to 3610 (OH), 1735 (carbonate), and 1710 cm$^{-1}$ (ester), $\delta$ (CDCl$_3$) include 5.40 (s, 1H), 3.94 (d, J 10 Hz, 1H), 3.77 (s, 3H) and 0.76 (d, J 7 Hz, 3H), m/z=670 (M+), from Factor A, 5-acetate 23-(2,2,2-trichloroethyl) carbonate (300 mg).

EXAMPLE 91

23-Deoxy Factor A, 5-methylcarbonate (57 mg)

$[\alpha]_D° +152°$ (c 0.6, CHCl$_3$), $\lambda_{max}$ (EtOH) 244.5 nm ($\epsilon$ 28,200), $\nu_{max}$ (CHBr$_3$) 3530 and 3460 (OH), 1740 (carbonate) and 1707 cm$^{-1}$ (ester), $\delta$ (CDCl$_3$) include 5.55 (s, 1H), 3.82 (s, 3H), 3.42 (d, J 10 Hz, 1H) and 0.69 (d, J 4 Hz, 3H), from 23-deoxy Factor A (90 mg) and methyl chloroformate (0.3 ml of 1M-solution in dichloromethane).

EXAMPLE 92

Factor A, 23-bromoacetate (190 mg)

$[\alpha]_D° +154°$ (c 0.93, CHCl$_3$), $\lambda_{max}$ (EtOH) 245 nm ($\epsilon$ 28,900), $\nu_{max}$ (CHBr$_3$) 3565 and 3500 (OH), and 1720 and 1715 cm$^{-1}$ $\delta$ =CDCl$_3$) include 5.41 (s, 1H), 4.3.93 (d, J10 Hz, 1H), 3.89 and 3.81 (ABq, J12 Hz, 2H) and 0.75 (d, J7 Hz, 3H), from, Factor A (306 mg) and bromoacetyl bromide (0.22 ml).

EXAMPLE 93

Factor A, 5-methyl carbonate, 22-bromoacetate (85 mg)

$[\alpha_D°+152°$(c 0.65, CHCl$_3$), $\lambda_{max}$(EtOH) 244.5 nm($\epsilon$29,600), $\nu_{max}$(CHBr$_3$) 3480(OH), 1742(Carbonate) and 1720 cm$^{-1}$(esters), $\delta$(CDCl$_3$) include 5.55(s, 1H), 3.97(m, 1H), 3.88 and 3.80(ABq, J12 Hz, 2H), 3.82(s, 3H) and 0.74 (d, J7 Hz, 3H), from Factor A, 23-bromoacetate (110 mg) and methyl chloroformate (0.3 ml of 1M-solution in dichloromethane).

EXAMPLE 94

Factor A, 23-chloroacetate (193mg)

$[\alpha]_D^{20}+162°$ (c 1.04, CHCl$_3$), $\lambda_{max}$(EtOH)245 nm($\epsilon$28,900), $\nu_{max}$(CHBr$_3$)3320 to 3620(OH), 1748(chloroacetate), and 1710 cm$^{-1}$(ester), $\delta$(CDCl$_3$) include 5.42(s, 1H), 4.28(m, 1H), 4.09 and 4.01(ABq, J15 Hz, 2H), 3.91(d, J10 Hz, 1H) and 0.73(d J7 Hz, 3H), m/z=688(M+, $^{35}$Cl), from Factor A (306 mg) and chloroacetyl chloride (0.2 ml)

EXAMPLE 95

Factor A, 5-methyl carbonate, 23-chloroacetate (53 mg)

$[\alpha]_D^{20}+162°$ (c 0.57, CHCl$_3$), $\nu_{max}$(EtOH) 245.5 nm ($\epsilon$28,800), $\nu_{max}$(CHBr$_3$) 3540 and 3470(OH), 1743(carbonate and chloroacetate) and 1710 cm$^{-1}$(ester), $\delta$(CDCl$_3$) include 5.55(s, 1H), 5.00(m, 1H), 4.10 and 4.02(ABq, J15 Hz, 2H), 3.92 (d, J10 Hz, 1H), 3.82(s, 3H) and 0.73(d, JHz, 3H), from Factor A, 23-chloroacetate (104 mg) and methyl chloroformate (0.3 ml of 1M-solution in dichloromethane).

EXAMPLE 96

Factor A, 5,23-dipropionate (387 mg)

$[\alpha]_D^{20}+157°$ (c 0.96, CHCl$_3$), $\epsilon_{max}$(EtOH) 244.5 nm ($\epsilon$30,200), $\nu_{max}$(CHBr$_3$) 3500(OH) and 1720 cm$^{-1}$(esters), $\delta$(CDCl$_3$) include 5.52(s, 1H), 3.93(d, J10 Hz, 1H), 2.43(q, J7 Hz,2H), 2.32 (q,J7 Hz,2H), 1.18(t, J7 Hz, 3H), 1.16(t, J7 Hz, 3H) and 0.70(d, J7 Hz, 3H), m/z=724(M+), from Factor A (613 mg) and propionic anhdride (0.5 m).

EXAMPLE 97

Factor A, 23-propionate (155 mg)

$[\alpha]_D°+168°$ (c, 1.03, CHCl$_3$), $\lambda_{max}$ (EtOH) 244.5 nm ($\epsilon$30,600), $\nu_{max}$(CHBr$_3$) 3550 and 3480(OH), and 1710 cm$^{-1}$Ester), $\delta$(CDCl$_3$) include 5.39(s, 1H), 4.27(m,1H), 3 91(d, J10 Hz, 1H), 2.31(q, J7 Hz, 2H), 1.14(t, J7 Hz, 3H) and 0.69(d, J7 Hz, 3H), m/z=668(M+), from Factor A, 5.23-dipropionate (327 mg).

EXAMPLE 98

Factor A, 5-methyl carbonate, 23-propionate (85 mg)

$[\alpha]_D°+172°$ (c 0.88, CDCl$_3$), $\lambda_{max}$ (EtOH) 245 nm ($\epsilon$28,700), $\nu_{max}$(CHBr$_3$) 3550 and 3460 (OH), 1740(carbonate), and 1718 and 1710 cm$^{-1}$(esters), $\delta$(CDCl$_3$) include 5.55(s, 1H), 4.94(m, 1H), 3.91(d, J10 Hz, 1H), 3.82(s, 3H), 2.32(q, J 7 Hz, 2H), 1.15(t, J7 Hz, 3H) and 0.70 (d, J7 Hz, 3H), from Factor A, 23-propionate (100 mg) and methyl chloroformate (0.3 ml of 1M-solution in dichloromethane).

EXAMPLE 99

Factor A. 5-(2,2,2-trichloroethyl) carbonate, 23-propionate (125 mg)

$[\alpha]_D°+110°$ (C, 1.02, CHCl$_3$), $\lambda_{max}$ (EtOH) 245 nm ($\epsilon$ 27,000) $\nu_{max}$ (CHBr$_3$) 3530 and 3470 OH), 1762 (carbonate) and 1712 cm$^{-1}$ (esters), $\delta$ (CDCl$_3$) include 5.60 (s, 1H), 4.90 and 4.75 (Abq, J12 Hz, 1H), 3.92 (d, J10 Hz, 1H), 2.31 (q, J7 Hz, 2H), 1.14 (t, J7, Hz, 3H) and 0.67 (d, J7 Hz, 3H), from Factor A, 23-propionate (100 mg) and 2,2,2,-trichloroethyl chloroformate (0.3 ml of 1M-solution in dichloromethane).

EXAMPLE 100

Factor A, 5-methyl carbonate, 23-ketone (830 mg)

$[\alpha]_D°+132°$ (c 0.82, CHCl$_3$), $\lambda_{max}$ (EtOH) 245 nm,($\epsilon$ 29,800). The i.r. and n.m.r. spectra were similar to those of the compound described in Example 88, from Fator A, 23-ketone (916 mg) and methyl chloroformate (0.23 ml).

EXAMPLE 101

Factor A, 5-ethylcarbonate, 23-ketone (65 mg)

$[\alpha]_D°+127°$ (c 0.5, CHCl$_3$). $\lambda_{max}$(EtOH) 245.5 nm ($\epsilon$29,600), $\nu_{max}$(CHBr$_3$) 3540 and 3480(OH), 1740(carbonate) and 1716 cm$^{-1}$ (ester and ketone), $\delta$(CDCl$_3$) include 5.57(s, 1H), 4.24 (q, J7 Hz, 2H), 3.70(d, J10 Hz, 1H), 2.50(s, 2H), 1.33(t, J7 Hz, 3H) and 0.87(d, J7 Hz, 3H), from Factor A, 23 -ketone (92 mg) and ethyl chloroformate (0.3 ml of 1M-solution in dichloromethane).

EXAMPLE 102

Factor A, 5-benzyl carbonate, 23-ketone (57 mg)

$[\alpha]_D° +99°$ (c 0.4m CHCl$_3$), $\lambda_{max}$ (EtOH) 245.5 nm ($\epsilon$ 29,600), $\nu_{max}$ (CHBr$_3$) 3600, 3550 and 3480 (OH) 1740 (carbonate and 1715 cm$^{-1}$ (ester and ketone), $\delta$(CDCl$_3$) include 7.5 to 7.2 (m, 5H), 5.57 (s, 1H), 5.21 (s, 2H), 3.70 (d J10 Hz, 1H), 2.49 (s, 2H) and 0.86d, J6 Hz, 3H), from Factor A, 23-ketone (92 mg) and benzyl chloroformate (0.05 ml).

EXAMPLE 103

Factor A, 5-(4-chlorobenzoate)

To a solution of Factor A (612 mg) in dry dichloromethane (2 ml) and pyridine (0.5 ml) was added 4-chlorobenzoyl chloride (210 mg), After 16 h at 23° the mixture was poured into ethyl acetate/water and the organic phase worked up for neutral material. The crude product was purified by chromatography was Merck Kieselgel 60, 230-400 mesh silica (50 g) using first dichloromethane and then dichloromethane-ether 19:1) as the eluting phases. This gave a yellow gum which after treatment with decolourizing charcoal afforded the title compound as a colourless foam (500 mg) ]$\alpha]_D^{23}$ +46° 23 +464 (c 0.80, CHCl$_3$); $\lambda_{max}^{(EtOH}$ 246 nm ($\epsilon_{max}$ 42,300); $\nu_{max}$ (CHBr$_3$) 1715 cm$^{-1}$ (ester) $\delta$(CDCl$_3$) includes 7.41 (d, 8 Hz, 2H) and 3.75 to 3.86 2H) and ca 3.8 (obscured m, 1H) (d, 2H), 8.00 (d, 2H) and 3.75 to 3.86 (m, 1H), m/z=750, 752 (M+, $^{35}$Cl and $^{37}$Cl).

EXAMPLE 104

23-Ketone Factor A, 5-(4-chlorobenzoate) (150 mg) which crystallized on trituration with diisopropyl ether m.p.t. 230°-232°, $[\alpha]_D^{23}+25°$ (c 0.48, CHCl$_3$); $\lambda_{max-EtOH}$ 245 (50,600) and 281.5 nm ($\epsilon_{max}$ 1,100), $\nu_{max}$ (CHBr$_3$) 3480 (OH) and 1718 cm$^{-1}$(esters and ketone), δ(CDCl$_3$) includes 8.00 (d, 8 Hz, 2H), 7.40 (d, 8 Hz,2H) and 2.50 (s, 2H). m/z=748, 750 (M+, $^{35}$Cl), from Factor A, 5-(4-chlorobenzoate) (420 mg).

EXAMPLE 105

5-Acetoxy-23-n-butoxy Factor A

Silver carbonate (1 g) was added to a solution of 5-acetoxy Factor A (325 mg) in dry ether, followed by iodobutane (0.5 ml) and silver perchlorate (550 mg). The mixture was stirred at room temperature for 20 h when collidine (0.5 l) was added. After stirring for a further 20 mn the mixture was filtered and the filtrate was washed successively with 2N hydrochloric acid, saturated aqueous sodium bicarbonate solution, and water. The dried organic phase was evaporated to near dryness and the oil was purified by chromatography over Merck Kieselgel 60 230-400 mesh (100 ml). Elution of the column with hexane:ethyl acetate (3:1) afforded the title compound as a colourless foam (276 mg, 78%) $[\alpha]_D^{22}+160°$ (c 0.94, CHCl$_3$) $\lambda_{max}$(EtOH) 245 nm ($\epsilon_{max}$ 28300); δ(CDCl$_3$) include 3.16 (m, 1H), 3.43 (m, 1H), 3.39 (m, 1H).

The compounds of Examples 106–108 were prepared in a similar manner to the compound of Example 30(a).

EXAMPLE 106

5-Acetoxy-23-cyclopentyloxy Factor A $[\alpha]_D^{21}+166°$ (c 1.60, CHCl$_3$), $\lambda_{max}$ (EtOH) 244 nm ($\epsilon_{max}$ 28,050); δ(CDCl$_3$) include 3.95 (m;1H), 3.45 (m;1H), 2.14 (s;3H), from 5-acetoxy Factor A and cyclopentyl bromide.

EXAMPLE 107

5-Acetoxy-23-isopropoxy Factor A.

$[\alpha]_D^{21}+169°$ (c 1.00, CHCl$_3$), $\lambda_{max}$ (CHBr$_3$) 3470 (OH), 1732 and 1710 cm$^{-1}$ (esters), δ(CDCl$_3$) include 5.5–5.6 (m; 2H), 3.93 (d 10 ; 1H), 3.5–3.7 (m; 2H), 3.53 (m, 1H), 2.16 (s; 3H), 1.13 (d6; 3 3H), 1.03 (d7; 6H), 0.71 (d 7: 3H), from 5-acetoxy Factor A and 2-iodopropane.

EXAMPLE 108

5-Acetoxy-23-cyclopropylmethoxy Factor A.

$[\alpha]_D^{21}+174°$ (c 1.74, CHCl$_3$) $\lambda_{max\ (Etoh)}$ 244 nm ($\epsilon_{max}$ 28 360) $\nu_{max}$ (CHBr$_3$) 3470 (OH),, 1732, 1710 (esters) and 998 cm$^{-1}$ (C-O) δ(CDCl$_3$) include 5.5–5.6 (m; 2H), 3.96 (d, 10; 1H), 3.49 (m; 1H), 3.37 (dd 6, 10;1H) 3.17 (dd 6.10; 1H), 2.16 (s; 3H), 0.76 d 7;3H), 0.44 (m; 2H), 0.22 (m; 2H), from 5-acetoxy Factor A and bromomethylcyclopropane.

EXAMPLE 109

5-t-Butyldimethylsilyloxy-23-methoxy Factor A

A solution of methylmagnesium iodide in ether (0.35 ml of 3 Molar solution) was added at room temperature under nitrogen to a magnetically stirred solution of 5-t-butyldimethylsilyloxy-Factor A 2.39 mg) in dry hexamethylphosphortriamide (18 ml) with effervescence. After 30 min iodomethane (0.4 ml) was added and the resultant mixture was stirred for 5 h, diluted with ether (100 ml) and washed liberally with water. The ether solution was then washed with brine (50 ml) and the dried organic phase was evaporated. The resultant foam (280 mg) was purified by chromatography over Merck Kieselgel 60 230≧400 mesh (80 ml). Elution with hexane:ethyl acetate (5:1) afforded the title compound as a colourless foam (46%) $[\alpha]_D^{21}+142°$ (c 1.13, CHCl$_3$) $\lambda_{max}$ (EtOH) 244 nm ($\epsilon_{max}$ 27900); $\nu_{max}$ (CHBr$_3$) 3460 (OH), 1708 (broad; ester) and 995 cm$^{-1}$ (C-O); δ(CDCl$_3$) include 4.42 (m;1H), 3.92 (d 10; 1H), 3.3–3.4 (m; 2H), 3.32 (s; 3H), 0.92 (s; 9H), 0.75 (d 7; 3H), 0.12 (s; 6H).

The compound of Example 110 was prepared in a similar manner:

EXAMPLE 110

5-t-Butyldimethylsilyloxy-23-n-propyloxy Factor A $[\alpha]_D^{21}+153°$ (c 1.16; CHCl$_3$), $\lambda_{max}$ (EtOH) 244 nm ($\epsilon_{max}$29950), $\nu_{max}$ (CHBr$_3$) 3460 (OH), 1705 (ester) and 995 cm$^{-1}$(C-O), δ (CDCl$_3$) include 4.44 (m; 1H), 3.96 (d 10; 1H) 3.56 (m; 1H), 3.45 (m; 1H), 3.14 (m; 1H), 0.93 (s; 9H), 0.75 (d 7; 3H), 0.13 (s; 6H), from 5-t-butyldimethylsilyloxy Factor A and 1-iodopropane.

EXAMPLE 111

Factor A 5-acetate 23-p-tolylthionocarbonate

A solution of Factor A 5-acetate (4.000 g) in dry dichloromethane (50 ml) and dry pyridine (4.9 ml ) under nitrogen was treated with p-tolylchlorothionoformate (3.7 ml) dropwise over a period of 10 minutes. The resulting dark solution was stirred at room temperature for 45 hrs. The solution was diluted with dichloromethane (200 ml), washed successively with 2N-hydrochloric acid, saturated sodium bicarbonate solution, water and saturated brine (2×200 ml), then dried (magnesium sulphate) and solvent was evaporated to give a dark green foam. This was redissolved in ethyl acetate (200 ml) and treated with activated charcoal. Filtration followed by evaporation afforded a pale green foam which was chromatographed on silica (Merck Kieselgel 60, particle size 0.040–0.063 mm, mesh 230–400 under atmospheric pressure eluting with hexane-ethyl acetate (2:1), to give the title oompound as a pale yellow foam (3.946 g). $\lambda_{max}$ (ethanol) 245 nm ($\epsilon$34200), $\nu_{max}$ (CHBr$_3$) 3620–3340 (OH) 1731 (acetate), 1710 cm$^{-1}$ (carbonyl), δ(CDCl$_3$) includes 6.81 (d,6 Hz,3H), 2.16 (s,3H), 2 36 (s,3H), 3.34 (m,1H), 6.99 (d,9 Hz,2H), 7.20 (d,9 Hz,2H).

EXAMPLE 112

23-deoxy-Factor A 5-acetate

A solution of Factor A 5-acetate 23-p-tolylthioncarbonate (10.194 g) in dry toluene (100 ml) was heated to reflux under nitrogen and treated with α-azo-bis-isobutyronitrile (509 mg). A solution of tri-n-butyltin hydride (10.25 ml) in dry toluene (60 ml) was added dropwise over a period of 25 minutes, maintaining the reflux conditions. The mixture was stirred for a further 25 mins, then cooled to room temperature and solvent was evaporated to give a yellow oil. This was dissolved in acetonitrile (600 ml) and washed with hexane. The solvent was evaporated to give a white foam which was chromatographed on silica (Merck Kieselgel 60, particle size 0.040–0.063 mm, mesh 230–400) eluting with hexane-ethyl acetate (4:1), to afford the title compound (2.442 g), $[\alpha]_D^{22}+144°$ (c 0.43 chloroform), $\lambda_{max}$ (ethanol) 245.5 nm (ξ29650), $\nu_{max}$ (CHBr$_3$) 3420–3340 (OH), 1732 (acetate), 1710 cm$^{-1}$ (carbonyl), δ(CDCl$_3$) includes 0.68 (d,5 Hz,3H), 2.16 (s,3H), 3.32 (m, 1H).

In a similar manner to the preparation of the corresponding Factor A derivatives above were prepared the Following Factor D derivatives of Examples 113–120.

EXAMPLE 113

5-Acetoxy Factor D (923 mg) $[\alpha]_D < +143.9°$ (c 0.9, CHCl$_3$). $\lambda_{max}^{EtOH}$239 (28,700) and 245 nm ($\epsilon_{max}$31,000); $\nu_{max}$(CHBr$_3$) 3490 )H) 1730 and 1710 (ester); $\delta$(CDCl$_3$) 0.81 (d, 7 Hz; 3H), 0.99 (d, 7 Hz; 3); 1.00 (t, 7 Hz; 3H) 1.53 (s; 3H), 1.59 (5; 3H), 1.75 (s; 3H), 1.6 (s; 3H), 3.32 (m; 1 H), 3.65 (m; 1H) 4.04 (d, 6 Hz;11H) and 5.53 (m; 2H). m/z=640 (M+), from Factor D (2.5 g) and acetic anhydride (0.47 ml).

EXAMPLE 114

5,23-Diacetoxy Factor D (286 mg)

m.p. 147–149° (rhombs from pentane in ether ($\alpha$)$_D^{21}$+152.6° (C 0.9, CHCl$_3$). $\lambda_{max}^{EtOH}$ 232.5 (21,500), 238 (26,600), and 244.5nm ($\epsilon_{max}$ 28,800); $\nu_{max}$(CHBr$_3$) 1720$^{-1}$ (ester); $\delta$ (CXCl$_3$) 0.72 (d, 6 Hz; 3H), 0.99 (d, 6 Hz; 3H), 1.01 (t, 7 Hz; 3H), 1.53 (s; 3H), 1.60 (s; 3H), 1.75 (s; 3H), 2.02 (s; 3H), 2.15 (s; 3H), 3.31 (m; 1H), 4.04 (d, 6 Hz, 1H), 4.91 (m; 1H) and 5.5 to 5.6 (m; 2H). m/x=682 (M+). From Factor D (439 mg) and acetic anhydride (0.25 ml).

EXAMPLE 115

23-Acetoxy Factor D (127 mg)

$[\alpha]_D^{21}$150° (c 0.5, CHCl$_3$), $\lambda_{max}^{EtOH}$238 (29, 200) and 244.5 nm ($\epsilon_{max}$ 15,600); $\nu_{max}$ (CHBr$_3$) 3300, 3590 (OH) and 1710 cm$^{-1}$ (ester); $\delta$ (CDCl$_3$) 0.72 (d, 7 Hz 3H), 0.99 (d, 7 Hz; 3H); 1.01 (t, 7 Hz; 3H) 1.53 (s; 3H) 160 (s; 3H), 1.86 (s; 3H), 3.26 (m; 1H), 3.95 (d, 6 Hz; 1H), 4.26 (t, 6 Hz; 1H) and 4.91 (m; 1H). m/z=640 (M+). From 5,23-diacetoxy Factor D (207 mg).

EXAMPLE 116

23-p-Tolyloxythiocarbonyloxy Factor D, 5-Acetate (610 mg)

$[\alpha]_D^{21}$132° (c 0.4, CHCl$_3$), $\lambda_{max}^{EtOH}$238.5 (34,800) and 244.5 nm ($\epsilon_{max}$ 35,400); $\nu_{max}$ (CHBr$_3$) 359 and 3560 (OH) and 1730 cm$^{-1}$ (ester); $\delta$ (CDCl$_3$) 0.81 (d, 7 Hz 3H), 0.99 (d, 7 Hz; 3H); 1.00 (t, 7 Hz; 3H), 1.53 (s; 3H) 1.61 (s; 3H), 1.75 (s; 3H), 2.15 (s; 3H), 2.36 (s, 3H), 3.33 (m; 1H), 3.98 (d, 10 Hz, 1H) 4.04 (d, 6 Hz; 1H), 5.5–5.6 (m; 2H), 6.98 (d, 9 Hz; 2H) and 7.19 (d, 9 Hz; 2H) m/z=790 (M+). From 5-diacetoxy Factor D (776 mg) and p-tolylchlorothionoformate (0.75 ml).

EXAMPLE 117

5-Acetoxy,23-deoxy Factor D (367 mg)

A portion of this sample was recrystallised from hexane to afford analytically pure material by HPLC m.p. 222°–224°, ($\alpha_D^{21}$+134° (c 0.9, CHCl$_3$), $\lambda_{max}^{EtOH}$245 nm ($\epsilon_{max}$32,400); $\nu_{max}$(CHBr$_3$) 3550, 3460 (H), 1735 and 1710 cm$^{-1}$ (ester); $\delta$(CDCl$_3$) 0.69 (d, 6 Hz; 3H), 1.00 (d, 6 Hz; 3H), 1.00 (t, 7 Hz; 3H), 1.53 (s; 3H), 1.59 (s; 3H), 1.76 (s; 3H), 2.14 (s, 3H) 3.31 (m; 1H), 3.44 (d, 10 Hz; 1H), 4.05 (d, 6 Hz; 1H) and 5.5-5.6 (m; 2H). m/z=624 (M+). From 5-acetoxy,23-p-tolyloxythiocarbonyloxy Factor D (582 mg).

EXAMPLE 118

23-deoxy Factor D (159 mg)

$[\alpha]_D^{21}$123° (c 0.5, CHCl$_3$), $\lambda_{max}^{EtOH}$244.6 nm ($\epsilon_{max}$ 28,300); $\nu_{max}$ (CHBr$_3$) 3550 and 3460 (OH) and 1705 cm$^{-1}$ (ester); $\delta$ (CDCl$_3$) 0.69 (d, 6 Hz; 3H), 1.00 (d, 6 Hz; 3H), 1.00 (6, 7 Hz; 3H), 1.53 (s; 3H), 1.59 (s; 3H), 1.87 (s; 3H), 3.26 (m; 1H), 3.44 (d, 10 Hz; 1H), 3.96 (d, 6 Hz; 1H) and 4.28 (t, 6 Hz; 1H). m/z=582 (M+). From 5-acetoxy,23-dihydro Factor D (231 mg).

EXAMPLE 119

5-Acetoxy,23-keto Factor D (152 mg)

m.p. 228°–230°, $[\alpha]_D^{21}$84° (c 0.6, CHCl$_3$), $\lambda_{max}^{EtOH}$244.5 nm ($\epsilon_{max}$ 31,100); $\nu_{max}$ (CHBr$_3$) 3500 (OH), 1732 and 1714 cm$^{-1}$ (ester and ketone); $\delta$ (CDCl$_3$) 0.86 (d, 6 Hz; 3H), 0.98 (d, 6 Hz; 3H), 1.00 (t, 7 Hz; 3H), 1.49 (s; 3H), 1.67 (s; 3H) 1.74 (s; 3H), 2.14 (s; 3H), 3.33 (m; 1H), 4.03 (d, 6 Hz; 1H) and 5.5–5.6 (m; 2H). m/z=638 (M+). From 5-acetoxy Factor D (336 mg).

EXAMPLE 120

23-Keto Factor D (59 mg)

$[\alpha]_D^{21}$84° (c 0.4, CHCl$_3$), $\lambda_{max}^{EtOH}$244.5 nm ($\epsilon_{max}$ 28,000); $\nu_{max}$ (CHBr$_3$) 3550 and 3550 (OH) and 1712 cm$^{-1}$ (ester and ketone); $\delta$ (CDCl$_3$) 0.86 (d, 6 Hz; 3H), 0.98 (d, 7 Hz; 3H), 1.00 (t, 7 Hz; 3H), 1.50 (s; 3H), 1.68 (s; 3H), 1.86 (s; 3H), 3.27 (m; 1H), 3.73 (d, 10 Hz; 1H), 3.95 (d, 6 Hz; 1H) and 4.27 (t, 6 Hz; 1H). From 5-acetoxy,23-keto Factor D (96 mg).

EXAMPLE 121

Factor A, 23-phenylacetate (240 mg) $[\alpha]_D^{20}$+140° (c 0.92, CHCl$_3$), $\nu_{max}$ (CHBr$_3$) 3550 and 3470 (OH) and 1730 cm$^{-1}$ (esters), $\delta$ (CDCl$_3$) include 7.32 (s, 5H), 5.0 (m, 1H), 4.29 (t, J7 Hz, 1H), 3.88 (d, J10 Hz, 1H), 3.62 (s, 2H) and 0.54 (d, J7 Hz, 3H), was prepared in a similar manner to the compound of Example 81 from Factor A (306 mg) and phenylacetyl chloride (0.33 ml).

EXAMPLE 122

23-Ethoxy Factor A

A solution of 5-acetoxy-23-ethoxy Factor A (806 mg) in methanol (18 ml) was cooled in an ice bath, 1N aqueous sodium hydroxide (1.3 ml) was added, and the light yellow solution was stirred in an ice bath for 1.25 h. The solution was diluted with ethyl acetate (80 ml), then washed successively with 1N hydrochloric acid, water and brine. The dried organic phase was evaporated and the resultant gum was purified by chromatography over Merck Keiselgel 60 silica 230–400 mesh (200 ml). Elution of the column with 15% ethyl acetate in dichloromethane afforded the title compound as a colourless foam (623 mg) $[\alpha]_D^{21}$+178° (c 1.13, CHCl$_3$) $\lambda_{max}$ (EtOH) 244 nm ($\epsilon_{max}$29,400); $\delta$ (CDCl$_3$) include 4.29 (t 7;1H), 3.65 (m;1H), 3.47 (m;1H), 3.26 (m;2H), 1.15 (t,7;3H).

The compounds of Examples 123–126 were prepared in a similar manner:

EXAMPLE 123

23-n-Butoxy Factor A (61%) was obtained as a colourless foam $[\alpha]_D^{21}$+161° (c 1.47, CHCl$_3$) $\lambda_{max}$ (EtOH) 244 nm ($\epsilon$ 33100); $\delta$ (CDCl$_3$) include 4.30 (t,7;1H), 3.60 (M;1H), 3.43 (M;1H), 3.17 (m;1H) from 5-acetoxy-23-n-butoxy-Factor A.

EXAMPLE 124

23-n-Propoxy Factor A (83%) was obtained a colourless foam $[\alpha]_D^{21}$+165° (c 1.01, CHCl$_3$), $\lambda_{max}$ (EtOH) 2.45 nm ($\epsilon$ 30,970), $\delta$ (CDCl$_3$) include 4.29 (t,7;H), 3.55 (m;p1H), 3.44 (m;1H), 3.13 (m;1H) from 5-acetoxy-23-n-propoxy Factor A.

EXAMPLE 125

23-Methoxy Factor A (66%) was obtained as a colourless foam [α]$_D^{21}$+175° (c 1.01, CHCl$_3$) λ$_{max}$ (EtOH) 244 nm (ε 19,100); δ (CDCl$_3$) include 4.29 (t,7;1H), 3.40 (m;1H), 3.33 (s;3H) from 5-acetoxy-23-methoxy Factor A.

EXAMPLE 126

23-Cyclopentyloxy Factor A (75%) was obtained as a colourless foam [α]$_D^{21}$+160° (c 1.65, CHCl$_3$) λ$_{max}$ (EtOH) 244 nm (ε 19,800); δ (CDCl$_3$) include 4.29 (t,7;1H), ca 3.96 (obscured m;1H), 3.95 (d,5;1H) 3.91 (d,10;1H), 3.46 (m;1H), 0.69 (d,7;3H) from 5-acetoxy-23-cyclopentyloxy Factor A.

EXAMPLE 127

(a) 5-Acetoxy-23-allyloxy Factor A

Silver salicylate (872 mg) was added to a solution of 5-acetoxy Factor A (207 mg) and allyl iodide (1.0 ml) in dry ether (25 ml) and the mixture was stirred at room temperature for 4 days, then filtered. The filtrate was evaporated to afford a yellow oil which was purified by chromatography over Merck Keiselgel 60, 230–400 mesh. Elution with dichloromethane:ethyl acetate (19:1) afforded the title compound as a colourless foam (105 mg), [α]$_D^{21}$+152° (c 1.00, CHCl$_3$), λ$_{max}$ (EtOH) 245 nm (ε, 28400), δ (CDCl$_3$) include 3.54 (m,1H), 4.14 (m,1H). The following compounds were prepared in a similar manner:

(b) 5-Acetoxy-23-n-propyloxy Factor A from 5-acetoxy Factor A and n-propyl iodide. Purification by chromatography over Merck Keiselgel 60, 230–400 mesh silica, eluting with hexane:ethyl acetate (3:1) afforded the title compound as a colourless foam [α]$_D^{22}$+160° (c 0.75, CHCl$_3$), λ$_{max}$ (EtOH) 245 nm, (ε, 27600) δ (CDCl$_3$) include 3.33 (s,3H), 3.39 (m,1H).

(c) 5-Acetoxy-23-methoxy Factor A from 5-acetoxy Factor A and methyl iodide. The title compound was obtained as a colourless foam [α]$_D^{22}$+159° (c 0.98, CHCl$_3$), λ$_{max}$ (EtOH) 245 nm (ε, 27600) δ (CXCl$_3$) include 3.33 (s,H), 3.39 (m,1H).

The following are examples of formulations according to the invention. The term 'Active Ingredient' as used hereinafter means a compound of the invention and may be for example the compounds of Examples 11, 14, 21, 27, 97, 122 or 123.

| Multidose parenteral injection | | |
|---|---|---|
| | % w/v | Range |
| Active Ingredient | 4.0 | 0.1–7.5% w/v |
| Benzyl alcohol | 2.0 | |
| Glyceryl triacetate | 30.0 | |
| Propylene glycol to | 100.0 | |

Dissolve the active ingredient in the benzyl alcohol and glyceryl triacetate. Add propylene glycol and make up to volume. Sterilise the product by conventional pharmaceutical methods, for example sterile filtration or by heating in an autoclave and package asseptically.

| Aerosol spray | | |
|---|---|---|
| | % w/w | Range |
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet Method of manufacture - wet granulation | |
|---|---|
| | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |

Microcrystalline cellulose to tablet core weight of 450 mg Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use Method of manufacture - dry granulation | |
|---|---|
| | mg |
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

| Veterinary intrammary injection | | | |
|---|---|---|---|
| | | mg/dose | Range |
| Active Ingredient | | 150 mg | 0.05–1.0 g |
| Polysorbate 60 | 3.0% w/w | | |
| White Beeswax | 6.0% w/w cr,3 | to 3 g | to 3 or 15 g |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary oral drench | | |
|---|---|---|
| | % w/v | Range |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | | |
|---|---|---|
| | % w/w | Range |
| Active Ingredient | 7.5 | 1–30% w/w |
| Saccharin | 25.0 | |
| Polysorbate 85 | 3.0 | |
| Aluminium distearate | 5.0 | |
| Fractionated coconut oil | to 100.0 | |

Disperse the aluminum distearate in the fractionated coconut oil and polysorbate 85 by heating. Cool to room temperature and disperse the saccharin in the oily vehicle. Dispense the active ingredient in the base. Fill into plastic syringes.

| Granules for veterinary in-feed administration | | |
|---|---|---|
| | % w/w | Range |
| Active Ingredient | 2.5 | 0.05–5% w/w |
| Calcium sulphate, hemi-hydrate | to 100.0 | |

Blend the Active Ingredient with the calcium sulphate. Prepare the granules using a wet granulation process. Dry using a tray or fluid-bed drier. Fill into the appropriate container.

| Emulsifiable Concentrate | |
|---|---|
| Active ingredient | 50 g |
| Anionic emulsifier (e.g. Phenyl sulphonate CALX) | 40 g |
| Non-ionic emulsifier (e.g. Syperonic NP13) | 60 g |

Aromatic solvent (e.g. Solvesso 100) to 1 liter. Mix all ingredients, stir until dissolved.

| Granules | | |
|---|---|---|
| (a) Active ingredient | 50 g | |
| Wood resin | 40 g | |
| Gypsum granules (20–60 mesh) to (e.g. Agsorb 100A) | 1 kg | |
| (b) Active ingredient | 50 g | |
| Syperonic NP13 | 40 g | |
| Gypsum granules (20–60 mesh) to | 1 kg. | |

Dissolve all ingredients in a volatile solvent e.g. methylene chloride, add to granules tumbling in mixer. Dry to remove solvent.

We claim:

1. A compound of formula (II)

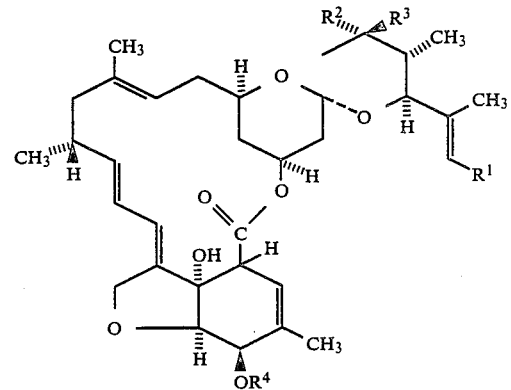

wherein $R^1$ is a methyl, ethyl or isopropyl group;

$R^2$ is a hydrogen atom or a group $OR^5$ and $R^3$ represents a hydrogen atom, or $R^2$ and $R^3$ together with the carbon atom to which they are attached represent a $>C=O$ group;

$OR^5$ is —OH, —$OCOR^6$, where $R^6$ is $C_{1-8}$ alkyl optionally substituted by halo, $C_{1-4}$ alkoxy, phenoxy or phenyl, $C_{3-6}$ cycloalkyl or phenyl; —$OCO_2R^{6a}$, where $R^{6a}$ is $C_{1-4}$ alkyl optionally substituted by halop; —$OCSOR^{6b}$, where $R^{6b}$ is phenyl optionally substituted by $C_{1-4}$ alkyl; —$OR^7$ where $R^7$ is $C_{1-4}$ alkyl optionally substituted by $C_{3-5}$ cycloalkyl, $C_{3-5}$ cycloalkyl or $C_{3-5}$ alkenyl; —$OSO_2R^8$, where $R^8$ is $C_{1-4}$ alkyl or phenyl optionally substituted by $C_{1-4}$ alkyl; or —$OCO(CH_2)_nCO_2R^9$, where $R^9$ is a hydrogen atom or a $C_{1-4}$ alkyl group and n represents zero, 1 or 2; and $OR^4$ is —OH, —$OCOR^{4a}$, where $R^{4a}$ is $C_{1-4}$ alkyl, optionally substituted by halo, phenoxy, or tri($C_{1-4}$ alkyl)silyloxy, phenyl or halophenyl; —$OCO(CH_2)_nCO_2R^9$, where $R^9$ is a hydrogen atom or a $C_{1-4}$ alkyl group and n represents zero, 1 or 2; —$OCO_2R^{4b}$, where $R^{4b}$ is $C_{1-4}$ alkyl optionally substituted by phenyl or halo; $C_{1-4}$ alkoxy; or tri($C_{1-4}$ alkyl)silyloxy;

excluding the compounds in which $R^2$ is —OH and $OR^4$ is —OH or $OCH_3$.

2. A compound according to claim 1 in which $R^2$ is a group $OR^5$.

3. A compound according to claim 1 in which $R^2$ and $R^3$ together with the carbon atom to which they are attached form a group $>C=O$.

4. A compound according to claim 1 in which $R^2$ and $R^3$ are both hydrogen atoms.

5. A compound according to claim 1 in which $R^1$ is an isopropyl group.

6. A compound according to claim 1 in which $R^2$ is a hydrogen atom or an ethoxy, n-propoxy, cyclopropylmethoxy, acetoxy, phenacetoxy, propionoxy, isobutyrionoxy or cyclopropanecarbonyloxy group and $R^3$ is a hydrogen atom, or $R^2$ and $R^3$ together with the carbon atom to which they are attached form a $>C=O$ group.

7. A compound according to claim 1 in which —$OR^4$ is a hydroxy, methoxy, acetoxy or methyloxycarbonyloxy group.

8. A compound according to claim 1 in which $R^1$ is an isopropyl group, $R^2$ is a hydrogen atom or an ethoxy, n-propoxy, acetoxy or propionoxy group and $R^3$ is a hydrogen atom or $R^2$ and $R^3$ together with the carbon atom to which they are attached form a >C=O group, and $OR^4$ is a hydroxy, acetoxy or methyloxycarbonyloxy group.

9. A compound according to claim 1 in which $R^1$ is an isopropyl group, $R^2$ is a hydrogen atom, $R^3$ is a hydrogen atom and $OR^4$ is a hydroxyl group.

10. A compound according to claim 1 in substantially pure form.

11. A compound according to claim 1 in which $R^2$ is a hydrogen atom or a hydroxy group or a group of formula —$OCOR^6$ where $R^6$ is a $C_{1-8}$ alkyl group optionally substituted by a $C_{1-4}$ alkoxy or phen($C_{1-6}$)alkyl; —$OCO_2R^6$ where $R^6$ is a $C_{1-4}$ alkyl group optionally substituted by one to three halogen atom; —$OCOCO_2H$, —$OR^7$ where $R^7$ is a $C_{1-4}$ alkyl group, $C_{3-5}$ cycloalkyl, allyl or cyclopropylmethyl group; or $R^2$ nd $R^3$ together with the carbon atom to which they are attached form a >C=O group.

12. A compound according to claim 1 in which $R^1$ is an isopropyl group, $R^2$ is a propionoxy group, $R^3$ is a hydrogen atom and —$OR^4$ is a hydroxyl group.

13. A compound according to claim 1 in which $R^1$ is an isopropyl group, $R^2$ and $R^3$ together with the carbon atom to which they are attached form a >C=O group, and —$OR^4$ is a hydroxyl group.

14. A compound according to claim 1 in which $R^1$ is an isopropyl group, $R^2$ is an ethoxy group, $R^3$ is a hydrogen atom and —$OR^4$ is a hydroxyl group.

15. A compound according to claim 1 in which $R^1$ is an isopropyl group, $R^2$ is a n-propoxy group, $R^3$ is a hydrogen atom and —$OR^4$ is a hydroxyl group.

16. A compound according to claim 1 in which $R^1$ is a methyl group, $R^2$ is an acetoxy group, $R^3$ is a hydrogen atom and —$OR^4$ is a hydroxyl group.

17. A compound according to claim 1 in which $R^1$ is an ethyl group, $R^2$ is an acetoxy group, $R^3$ is a hydrogen atom and —$OR^4$ is a hydroxyl group.

18. A compound according to claim 1 in which $R^1$ is an isopropyl group, $R^2$ is an acetoxy group, $R^3$ is a hydrogen atom and —$OR^4$ is a hydroxyl group.

19. A pharmaceutical composition for administration to a human or animal subject containing an antibiotic effective amount of at least one compound as claimed in claim 1 together with an acceptable carrier.

20. A pharmaceutical composition for administration to a human or animal subject containing an antibiotic effective amount of at least one compound as claimed in claim 15 together with an acceptable carrier.

21. A pesticidal composition for eradication of insect, acarine and nemotode pests containing a pesticidal effective amount of at least one compound as claimed in claim 1 and a pesticidally acceptable carrier.

22. A pesticidal composition for eradication of insect, acarine and nematode pests containing a pesticidal effective amount of a compound as claimed in claim 15 and a pesticidally acceptable carrier.

23. A method of combating infection or infestations which comprises applying to insect, acarine or nematode pests, or to a location thereof, an effective amount to combat said infection or infestations of one or more compounds according to claim 1.

24. A method of combating infection or infestations which comprises applying to a fungus or a location thereof an effective amount to combat said infection or infestations of one or more compounds according to claim 1.

25. A method of treating a human or animal subject having an ectoparasitic condition comprising administering to the human or animal subject an antiparasitic effective amount of one or more of the compositions according to claim 19.

26. A method of treating a human or animal subject having an endoparasitic condition comprising administering to the human or animal subject an antiparasitic effective amount of one or more of the compositions according to claim 19.

27. A method for combating insect, acarine or nematode pests in agriculture, horticulture or forestry, which comprises applying to plants or other vegetation or a location thereof an effective amount of one or more compositions according to claim 21.

* * * * *

UNITED STATES PATENT AND TRADEMARK OFFICE
CERTIFICATE OF CORRECTION

PATENT NO. : 4,978,675

DATED : December 18, 1990

INVENTOR(S) : John B. Ward et al

It is certified that error appears in the above-identified patent and that said Letters Patent is hereby corrected as shown below:

Col. 48, lines 1-17, (claim 1) in the formula change

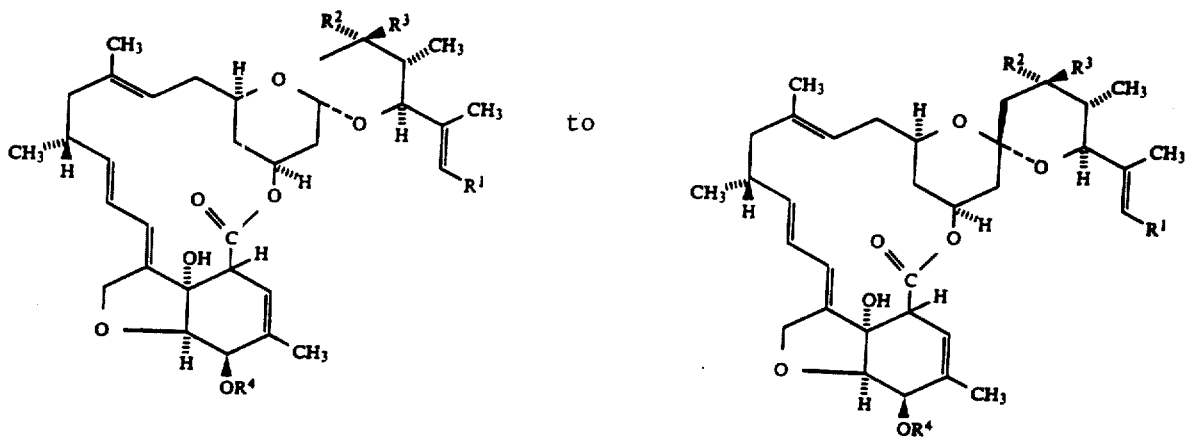 to 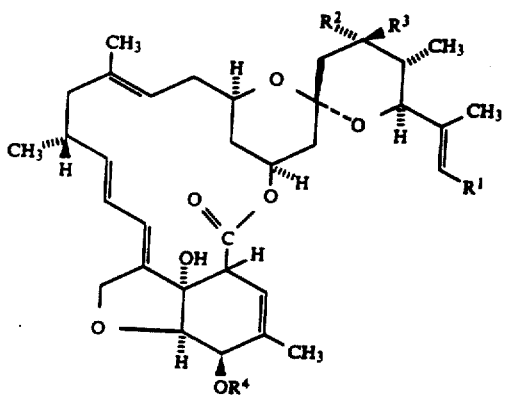

Signed and Sealed this

Twenty-seventh Day of October, 1992

Attest:

DOUGLAS B. COMER

Attesting Officer    Acting Commissioner of Patents and Trademarks